United States Patent
Wagner et al.

(10) Patent No.: US 8,563,501 B2
(45) Date of Patent: *Oct. 22, 2013

(54) MATERIAL FOR FACILITATING THERMAL TREATMENTS OF BIOLOGICAL TISSUES AND METHOD OF ENERGY TARGETING LEADING TO THERMAL TREATMENT OF BIOLOGICAL TISSUES

(71) Applicant: Clean Technology International Corporation, Pensacola, FL (US)

(72) Inventors: Anthony S. Wagner, Santa Fe, NM (US); Mark DeSantis, West Islip, NY (US)

(73) Assignee: Clean Technology International Corporation, Pensacola, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/663,212

(22) Filed: Oct. 29, 2012

(65) Prior Publication Data

US 2013/0053932 A1      Feb. 28, 2013

Related U.S. Application Data

(63) Continuation of application No. 13/311,025, filed on Dec. 5, 2011, now Pat. No. 8,299,014, which is a continuation of application No. 12/361,453, filed on Jan. 28, 2009, now Pat. No. 8,071,534.

(51) Int. Cl.
    *A61K 31/00*      (2006.01)

(52) U.S. Cl.
    USPC ................ 514/1; 977/773; 977/775; 977/778

(58) Field of Classification Search
    USPC ................................ 514/1; 977/773, 775, 778
    See application file for complete search history.

(56) References Cited

U.S. PATENT DOCUMENTS

| | | | |
|---|---|---|---|
| 4,138,998 A | 2/1979 | Nowogrodzki | |
| 7,901,653 B2 | 3/2011 | Wagner | |
| 7,922,993 B2 | 4/2011 | Wagner | |
| 8,299,014 B2 * | 10/2012 | Wagner et al. | 514/1 |
| 2011/0189076 A1 | 8/2011 | Wagner | |

OTHER PUBLICATIONS

Baeraky, Thoria A., "Microwaves Absorption in Lead Molybdenum Phosphate Glasses at Low Temperature," Egypt. J. Solids, 2006, pp. 175-180, vol. 29, No. 1. (6 pages).

Sherar et al., Article Outline for "Interstitial Microwave Thermal Therapy for Prostate Cancer: Method of Treatment and Results of a Phase I/II Trial," The Journal of Urology, Nov. 2001, vol. 166, Issue 5. (3 pages).

Simon et al., "Microwave Ablation: Principles and Applications," RadioGraphics, Oct. 2005, pp. s69-s83, vol. 25, Special Issue. (16 pages).

Webb et al., Abstract of "Microwave Absorption by Normal and Tumor Cells," Science, Oct. 1, 1971, vol. 174, No. 4004. (1 page).

* cited by examiner

*Primary Examiner* — Raymond Henley, III
(74) *Attorney, Agent, or Firm* — Russell D. Culbertson; The Culbertson Group, P.C.

(57) ABSTRACT

A method includes positioning an effective amount of a thermal target material at a treatment site of a patient. The treatment site, that is, the location of the thermal target material, comprises a location adjacent to biological tissue to be treated. The thermal target material includes carbon molecules preferably in a carrier fluid. Regardless of the particular structure of the carbon, the carbon molecules in the material heat very rapidly in response to incident microwave radiation and radiate heat energy. The heat energy radiated from an effective amount of the thermal target material when subjected to an effective quantity of microwave energy causes localized heating around the thermal target material. This localized heating may be applied for therapeutic purposes. However, the microwave radiation necessary to produce therapeutically effective heating is insufficient to cause cellular damage in the biological tissue by direct absorption in the tissue.

20 Claims, 17 Drawing Sheets

MATERIAL FOR FACILITATING THERMAL TREATMENTS OF BIOLOGICAL TISSUES AND METHOD OF ENERGY TARGETING LEADING TO THERMAL TREATMENT OF BIOLOGICAL TISSUES

CROSS-REFERENCE TO RELATED APPLICATION

This application is a continuation of U.S. patent application Ser. No. 13/311,025, filed Dec. 5, 2011, and entitled "Material For Facilitating Thermal Treatments of Biological Tissues and Method of Energy Targeting Leading To Thermal Treatment of Biological Tissues," now U.S. Pat. No. 8,299,014, which is a continuation of U.S. patent application Ser. No. 12/361,453, filed Jan. 28, 2009, and entitled "Material for Facilitating Thermal Treatments of Biological Tissues and Method of Energy Targeting Leading to Thermal Treatment of Biological Tissues," now U.S. Pat. No. 8,071,534. The Applicants claim the benefit of each of these prior applications under 35 U.S.C. §120. The entire content of each of these prior applications is incorporated herein by this reference.

TECHNICAL FIELD OF THE INVENTION

The invention relates to therapeutic uses of thermal energy. In particular, the invention encompasses a material that rapidly absorbs certain incident electromagnetic radiation and emits heat energy that may be used to damage diseased biological cells or enhance biological processes in biological tissues. The invention also encompasses methods for providing therapeutic thermal treatments for biological tissues.

BACKGROUND OF THE INVENTION

It is known that biological cells may be damaged by raising their temperature to approximately 40° C. to 46° C. Hyperthermal treatment, that is, applying temperatures in the range of 40° C. to 46° C. to localized areas of the body has been considered for ablating diseased biological tissue, particularly cancer cells. The application of heat has also been shown to enhance certain biological processes, particularly biological processes associated with healing tissue. Thus low-level heat energy has been applied to areas of damaged tissue in order to encourage biological repair processes.

Microwave energy has been considered for heating biological tissues both for hyperthermal treatment to ablate diseased biological tissues and for other therapeutic purposes such as for enhancing biological processes. U.S. Pat. No. 4,138,998 discusses various uses of microwave energy for therapeutic purposes. A problem with using microwave energy for therapeutic applications is that the microwave energy not only heats the intended target of the treatment, that is, the diseased tissue or the tissue undergoing repair processes, but also adjacent biological tissue. This is particularly a problem in hyperthermal treatments because it can cause excessive damage to healthy tissue in addition to the diseased tissue.

SUMMARY OF THE INVENTION

The present invention provides a material having unique electromagnetic radiation absorption properties. In particular, the material heats rapidly in response to incident electromagnetic radiation in the microwave spectrum and radiates heat energy by conduction and by the emission of infrared radiation. The heating from heat energy radiated from a material according to the present invention is sufficiently rapid as compared to heating in biological tissues in response to the incident microwave radiation to produce therapeutic heating from the material before undesirable heating occurs in the biological tissue from direct absorption of microwave radiation by the biological tissue. Thus materials according to the invention may be employed as a thermal treatment material that may be positioned either within or without a patient's body to administer a desired thermal treatment. The material according to the invention (hereinafter "thermal target material") may be positioned with respect to a patient's body so that when the material is subjected to electromagnetic radiation (hereinafter "EMR") in a desired wavelength range, at a desired power density, and for a desired period of time, the thermal target material provides localized heating sufficient to produce a desired therapeutic effect. The therapeutic effect may be to damage diseased cells in the biological tissue or to enhance a biological process in the tissue such as bone repair.

A method according to one preferred form of the invention for treating biological tissues includes positioning an effective amount of a thermal target material at a treatment site of a patient. The treatment site, that is, the location of the thermal target material, comprises a location adjacent to biological tissue to be treated. Thus the thermal target material may be placed, for example, in a tumor or other mass of biological tissue to be treated, and/or at the surface of a tumor or other mass of biological tissue. The proximity between the thermal target material and the biological material to be treated must be such that the heat released from the thermal target material due to the incident EMR heats the intended biological tissue without producing excessive heating in any substantial amounts of other nearby biological tissue. According to one preferred form of the invention, the thermal target material includes a low-hydrogen, nanostructured carbon preferably in a carrier fluid. By "nanostructured carbon" it is meant that the carbon is covalently bonded to form a structure such as a sphere, tube, or other regular structure. As will be discussed further below, it is believed that only carbon material having a low hydrogen content exhibits the desired EMR absorption properties and heat releasing properties. This low-hydrogen carbon material may be produced in a liquid reactant process described below. Regardless of the particular structure of the carbon and the manner in which the carbon is produced, the carbon molecules in the material have microwave absorption properties such that a mixture of the carbon material in water at a concentration of 0.0277 moles per 100 milliliters of water reaches the boiling temperature of the water in approximately 52.3% of the time required for 100 milliliters of the water to reach its boiling temperature in response to microwave radiation at 2.45 GHz at the EMR power level generated by a 1500 watt domestic microwave oven.

The carbon employed in the thermal target material according to the invention absorbs the incident microwave radiation and emits EMR in the infrared spectrum in response to the absorption of the microwave radiation. It is believed that this emission of infrared radiation is responsible for the bulk of the heating produced by the thermal target material although some heating by conduction undoubtedly occurs. It is further believed that the microwave absorption and heat emission properties of the carbon molecules employed in the present treatment process are related to the absence or at least low level of chemically bonded hydrogen in the carbon molecules. This low-hydrogen carbon is produced according to the reactant liquid processes described in U.S. patent application Ser. Nos. 10/887,695, 10/919,069, 11/025,717, 11/173,419, and 11/430,743, by the present Applicant, Anthony Wagner. The entire content of each of these U.S. patent applications is incorporated herein by this reference.

An "effective amount of the thermal target material" is an amount that will produce the desired heating in the desired biological tissue given the constraints on the amount of microwave energy that may be used as will be discussed below. Although an effective amount of thermal target material will vary depending upon the tissue to be treated in an application and the effect to be produced, it is believed that an effective amount of the thermal target material will include at least $1.18 \times 10^{-6}$ grams nanostructured carbon material which is substantially free of chemically bound hydrogen where the treatment site is a site within a mass of tissue to be treated. A suitable thermal target material may include low-hydrogen, nanostructured carbon in water at a concentration of at least $2.77 \times 10^{-4}$ moles per milliliter of water. Various types of viscosity enhancing agents may be used together with the carrier fluid to help hold the nanostructured carbon in suspension evenly distributed through the thermal target material.

Once the thermal target material is properly positioned at the treatment site, a treatment method according to the present invention includes directing an effective quantity of microwave energy to the thermal target material. As used herein and the accompanying claims, an "effective quantity" of microwave energy is a quantity at a given wavelength that is sufficient to heat tissue adjacent to the treatment site to a treatment temperature by heat energy radiation from the thermal target, but without increasing the temperature of nearby tissue to the treatment temperature. An "effective quantity" of microwave energy is low enough both in terms of instantaneous power level and cumulative value that the microwaves which are not absorbed by the thermal target material do not unduly heat the biological tissue by direct absorption in the biological tissue.

The treatment temperature used in methods according to the present invention will depend upon the effect desired in the biological tissue to be treated. Where the biological tissue comprises diseased tissue to be ablated, such as a cancerous tissue, the treatment temperature comprises a temperature sufficient to kill the cells of the tissue. Such a treatment temperature may be in the range of approximately 40° C. to 46° C. to denature the tissue to be treated. However, lower treatment temperatures may be used to enhance biological repair processes in tissue such as bone tissue for example.

A thermal target material for use in the above-described treatment includes preferably the low-hydrogen, nanostructured carbon having the above-described microwave absorption properties in a suitable carrier fluid such as water, preferably with a viscosity enhancing agent.

These and other advantages and features of the invention will be apparent from the following description of the preferred embodiments, considered along with the accompanying drawings.

DESCRIPTION OF PREFERRED EMBODIMENTS

The following description of preferred embodiments is divided into three parts. The first part will describe an apparatus and method for producing low-hydrogen, nanostructured carbon that may be used in a thermal target material according to the invention. The second part comprises a description of thermal target materials according to the present invention in terms of the physical structure and physical properties of their constituents, particularly their reaction to incident microwave radiation. The third and final part of the description of preferred embodiments will provide a description of how the thermal target materials may be used to provide therapeutic treatments according to the present invention.

Apparatus and Method for Producing Low-Hydrogen Carbon

A thermal target material according to the present invention preferably includes a carbon material that is substantially devoid of hydrogen and other impurities. The preferred method for producing the carbon material utilizes a reactant liquid to generate isolated carbon ions which may then elude from the reactant liquid into a suitable atmosphere which isolates the carbon ions from other materials that could react with the carbon ions. The eluded carbon ions then form the desired carbon molecules, preferably nanostructured carbon.

Figure 1:
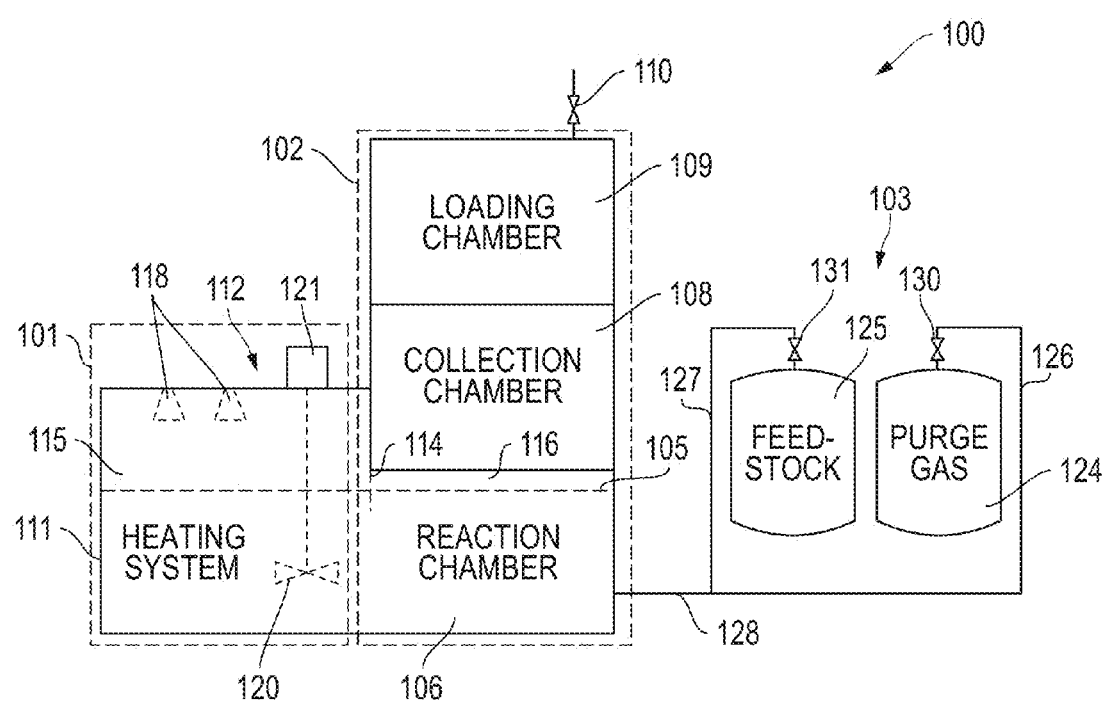
FIG. 1 is a diagrammatic representation of an apparatus that has been employed to produce spherical carbon nanostructures that may be employed in a thermal target material according to the present invention.

Referring to the diagrammatic representation of FIG. 1, an apparatus 100 for producing the desired nanostructured carbon, thermal target material includes a number of components that can be separated generally into three interrelated systems, a heating system shown in dashed box 101, a nano structure production and collection system ("production system") shown in dashed box 102, and an injection system shown generally at reference numeral 103. A reactant liquid, the surface level of which is shown at 105 in FIG. 1, is heated in heating system 101 and circulated between that system and a reaction chamber 106 of production system 102. Injection system 103 allows a stream of feedstock material and/or purge gas to be injected into reaction chamber 106 at a point below the level 105 of reactant liquid in the reaction chamber. In addition to reaction chamber 106, production system 102 further includes a collection chamber 108 and a loading chamber 109.

In the operation of apparatus 100, the carbon-bearing feedstock material injected into reaction chamber 106 below the surface level 105 of the reactant liquid in the reaction chamber, reacts quickly with the reactant liquid to produce chemically excited carbon ions containing one or two carbon atoms, depending upon the nature of the feedstock. The chemically excited carbon ions together with materials such as hydrogen released from the feedstock molecules and together with any purge gas atoms traverse the surface 105 of the reactant liquid in reaction chamber 106 and flow up into collection chamber 108. Above the reactant liquid and in collection chamber 108, the carbon ions chemically combine with other carbon ions to form carbon nanostructures and may collect on removable collection surfaces in the collection chamber. These collection surfaces will be shown and described further below in connection with FIGS. 2, 3, 5 and 6. Other atoms such as hydrogen atoms and purge gas atoms, eventually escape through a pressure relief valve 110 associated with loading chamber 109. After a desired collection period, the collection surfaces (not shown in FIG. 1) are removed from collection chamber 108 and cooled in loading chamber 109. Ultimately, the collection surfaces are removed from loading chamber 109, and the carbon nanostructures that have collected on the collection surfaces are removed from those surfaces. Further details of the operation of apparatus 100 will be described below in connection with FIGS. 2-6.

Reaction chamber 106 comprises a vessel suitable for containing a bath of a desired reactant liquid. The particular reactant liquid used in the examples described below comprises substantially pure liquid aluminum (99% aluminum by mass composition) at a temperature of approximately 1650° F. (between about 1642° F. and 1655° F.), and the vessel included in reaction chamber 106 is lined with a suitable refractory material which will not react with the liquid aluminum. Heating system 101 supplies the heat necessary to at least keep the reactant liquid at the desired temperature necessary to produce the desired reaction with the feedstock and chemically excite the resulting carbon ions to the desired valence level. Thus heating system 101 also includes a vessel 111 adapted to contain the reactant liquid and apply heat to the liquid to maintain the desired temperature in the liquid. A circulation device 112 is also preferably associated with heating system 101 and/or reaction chamber 106 to provide the desired circulation between the vessel included in the reaction chamber and the vessel associated with the heating system 101. In the preferred arrangement shown in FIG. 1, the heating system vessel 111 and the vessel making up reaction chamber 106 comprise essentially a single vessel separated by a baffle 114 that forms a barrier between a heating area 115 associated with heating system 101 and an area 116 above the reactant liquid level 105 in reaction chamber 106. The heating system 101 shown in FIG. 1 includes burners 118 for burning a suitable fuel to heat the material on the heating system side of baffle 114. The circulation device 112 shown in FIG. 1 includes a stirring element 120 which is driven by a motor 121 to provide the desired circulation under baffle 114.

The invention is not limited to the particular arrangement of heating system 101 and reaction chamber 106 shown in FIG. 1. For example, rather than heating the reactant liquid with combustible fuels as shown in FIG. 1, electrical induction heating or any other suitable heating arrangement or combination may be used to hold the reactant liquid at the desired temperature. In any case, the initial heating of the reactant liquid may be accomplished in heating system (such as system 101) or in a separate system (not shown) which feeds the pre-heated reactant liquid into the heating system. Furthermore, processes according to the present invention may be performed in a system in which the reaction chamber includes a vessel separate from the vessel associated with the heating system and in which a suitable connection between the separate vessels allows the desired circulation of the reactant liquid between the vessels. Where electrical heating arrangements are used to heat the reactant liquid, the heating may in fact occur in at least a portion of the reaction chamber itself, and thus a separate heating vessel may not be required. The present invention encompasses any arrangement by which the desired reactant liquid may be held at the desired temperature for reacting the feedstock material as will be described further below.

Injection system 103 includes a purge gas vessel 124 and a feedstock vessel 125 connected by suitable conduits 126 and 127, respectively, to an injection conduit 128. The flow of material through conduits 126 and 127 is controlled by control valves 130 and 131, respectively. Injection conduit 128 terminates at reaction chamber 106 so that materials from the vessels 124 and 125 may be injected into the liquid reactant material in the reaction chamber. Purge gas vessel 124 preferably contains a suitable inert purge gas such as argon which may be continuously injected into the system to prevent the reactant liquid from flowing into injection conduit 128. The purge gas is also used to purge the system of air as will be discussed below in connection with FIGS. 2 and 3. Feedstock vessel 125 contains the material that is to be reacted with the reactant liquid in reaction chamber 106 to produce chemically excited carbon ions which combine in the system to produce the desired carbon nano structures. It will be appreciated that the injection system 103 shown in FIG. 1 is shown only diagrammatically and that other valves and control devices may be included in the various conduits to direct feedstock and/or purge gas into reaction chamber 106 as desired according to the invention.

Figure 3:
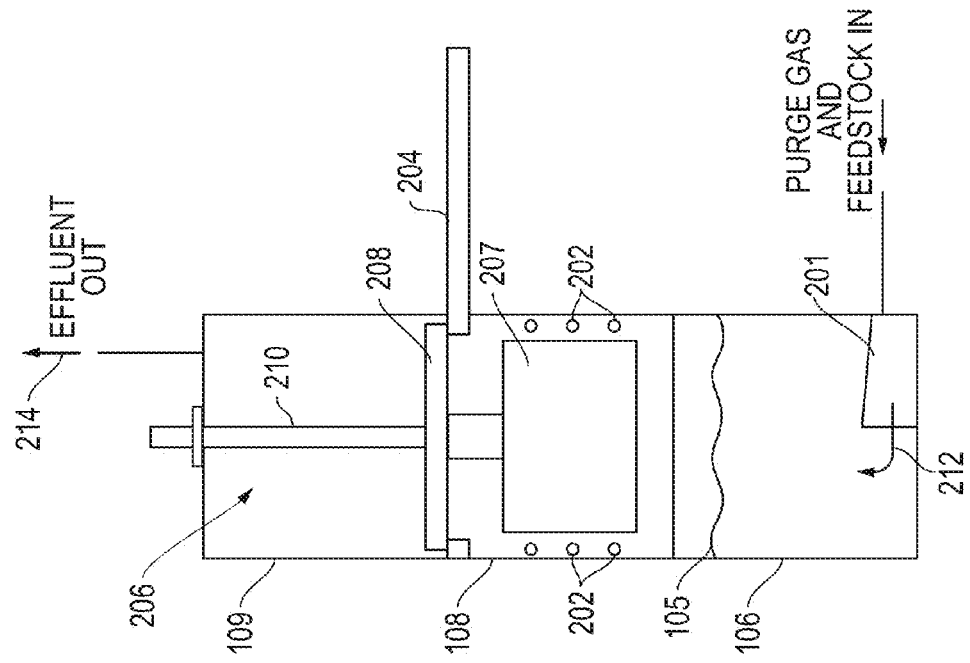
FIG. 3 is a diagrammatic representation similar to FIG. 2, but showing the condition of the apparatus when it is producing and collecting carbon nano structures.
Figure 2:
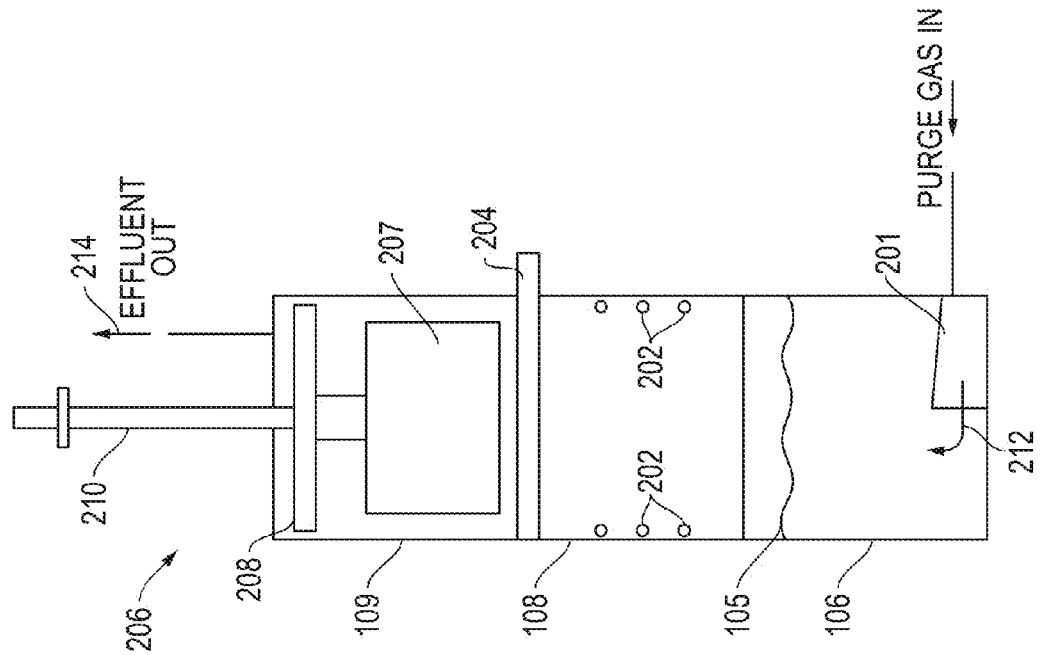
FIG. 2 is a diagrammatic representation of an apparatus for producing carbon nanostructures and showing the relationship between a reactant liquid bath, collection chamber, loading chamber, and collection structure when the apparatus is being prepared to receive the collection structure in position to collect carbon nano structures.

Further details regarding production system 102 may be described in connection with FIGS. 2 and 3. In particular, FIGS. 2 and 3 show a reaction tunnel structure 201 in reaction chamber 106, heater elements 202 in collection chamber 108, and an insulating slide door 204 made of steel or other suitable material interposed between the collection chamber and loading chamber 109. FIGS. 2 and 3 also show a collection/recovery arrangement shown generally at reference numeral 206. Collection/recovery arrangement 206 includes a collection structure 207 and an insulating plate 208 both connected to a manipulating structure 210.

Reaction tunnel structure 201 is included in the system to help increase the contact time between the feedstock material and reactant liquid and thereby ensure the desired decomposition and chemical excitation of the feedstock material. Reaction tunnel 201 also causes the input material to rise through the reactant liquid generally in the center of reaction chamber 106. The purge gas and/or feedstock injected into reaction chamber 106 follows the path generally shown at arrow 212 and FIGS. 2 and 3. Reaction tunnel 201 preferably comprises an inverted U-shaped structure formed from a suitable refractory material or having a refractory material exterior to withstand contact with the reactant liquid in reaction chamber 106.

Heater elements 202 are included in collection chamber 108 to help control the temperature within the collection chamber and the temperature of the collection structure as will be described further below. In one preferred arrangement, heater elements 202 comprise electrical resistance heater elements that extend along one or more sides of collection chamber 108. Although not shown in FIGS. 2 and 3, it will be appreciated that a suitable power supply supplies electrical power to heater elements 202 as required to control the temperature in the collection chamber 108 and collection structure 207.

Collection structure 207 is included in the production system 102 to provide appropriate collection surfaces on which carbon nano structures may collect according to the present invention. Further details of one preferred collection structure will be described in connection with FIGS. 5 and 6. It will be noted by comparing FIGS. 2 and 3 that collection structure 207 may reside in two different positions in the operation of production system 102. FIG. 2 shows collection structure 207 in an uppermost position in which it is fully contained in loading chamber 109. FIG. 3 shows collection structure 207 in its lowermost position in which it is fully contained in collection chamber 108. Manipulating structure 210 is included in the collection/recovery arrangements 206 to allow collection structure 207 to be positioned alternatively in the uppermost position shown in FIG. 2 and the lowermost position shown in FIG. 3. Insulating plate 208 is included in collection/recovery arrangements 206 to help insulate the loading chamber 109 from the elevated temperatures in collection chamber 108 when collection structure 207 is in its lowermost position shown in FIG. 3. Any suitable material such as spun ceramic wool may be used for insulating plate 208.

Figure 4:
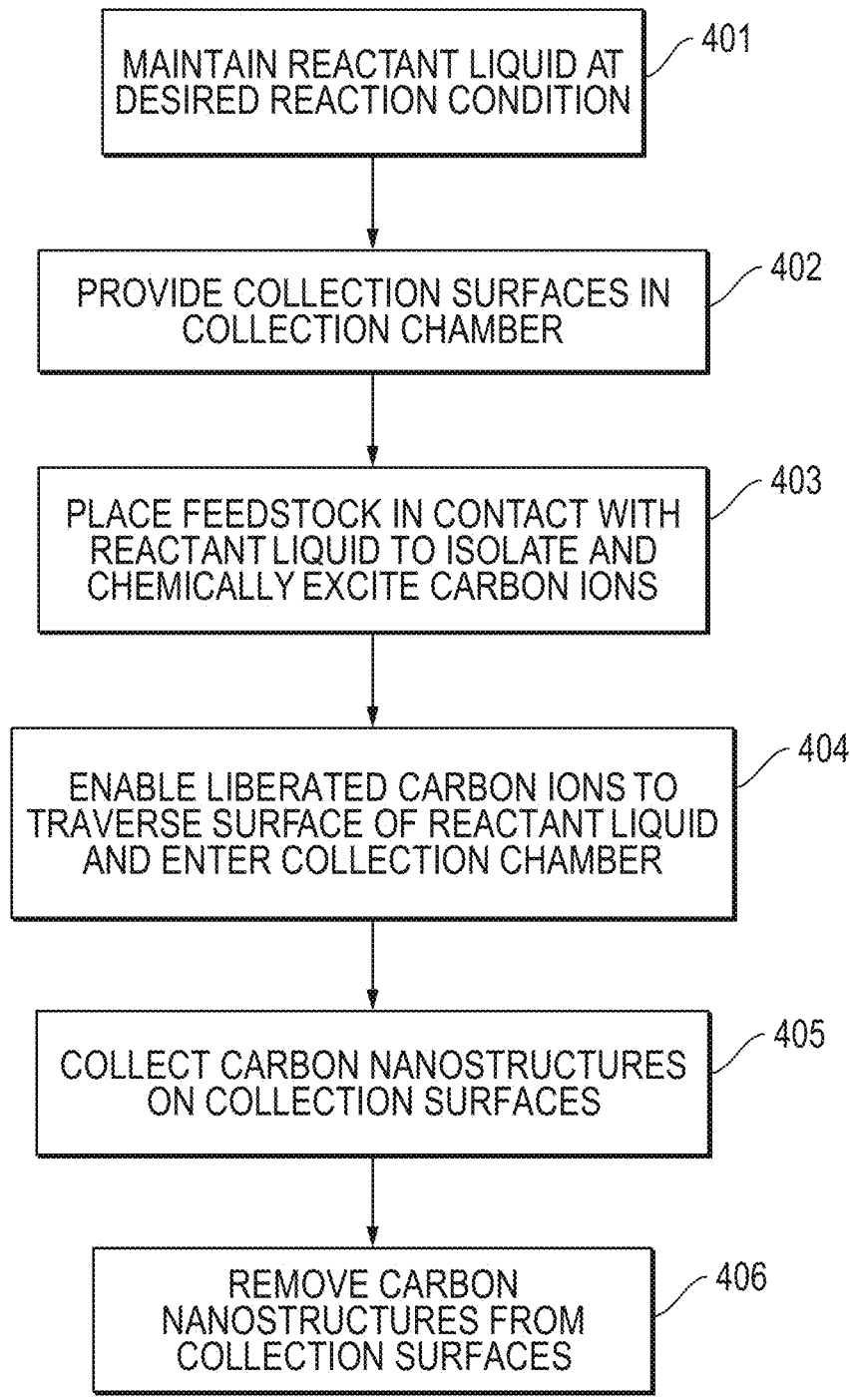
FIG. 4 is a process flow chart showing a process for producing spherical carbon nanostructures according to one preferred form of the present invention.

Processes for producing a nanostructured carbon that may be used in a thermal target material according to the present invention may be described with reference to the process flow chart shown in FIG. 4 and with reference to the example production system 102 shown in FIGS. 2 and 3. Referring first to FIG. 4, one preferred process includes maintaining a reactant liquid in a desired reactant condition as indicated at process block 401. This desired reactant condition is one in which the feedstock will react with the reactant liquid to chemically separate carbon atoms from other constituents in the feedstock material and chemically excite the resulting carbon ions. As shown at process block 403 in FIG. 4, the preferred process includes placing a suitable carbon-bearing feedstock in contact with the reactant liquid in the desired reactant condition to produce and chemically excite the carbon ions. These liberated carbon ions are then allowed to traverse a surface of the reactant liquid and enter a collection chamber as shown at process block 404. As indicated at process block 405 in FIG. 4, carbon nanostructures are collected on collection surfaces in the collection chamber. These collection surfaces may be provided as indicated at process block 402 in FIG. 4. The collected carbon nanostructures are ultimately removed from the collection surfaces as shown at process block 406.

Referring now to FIG. 2, manipulating arrangement 210 is initially held in its uppermost position for each cycle of operation, with insulating door 204 closed to help isolate loading chamber 109 from the heat associated with the reactant liquid held in reaction chamber 106. In this position, the airlock door (not shown in the figures) associated with loading chamber 109 may be opened to insert collection structure 207 on the receiving structure associated with manipulating arrangement 210, so that the collection structure resides in the position shown in FIG. 2. One preferred receiving structure which allows the collection structure 207 to be removably positioned on manipulating structure 210 will be described below in connection with FIGS. 5 and 6. Once the airlock door associated with loading chamber 109 is closed, the purge gas which is preferably continuously injected into reaction chamber 106 through injection conduit 128 eventually displaces air that has entered loading chamber 109 in the course of loading collection structure 207 to the position shown in FIG. 2. It is noted that insulating door 204 does not provide a gas tight seal between collection chamber 108 and loading chamber 109 when the insulating door 204 is closed, and thus the argon gas preferably continuously injected through injection conduit 128, may continue to flow into loading chamber 109 even when the insulating door is closed in the position shown in FIG. 2.

Once the air is purged from loading chamber 109, production system 102 is ready to be placed in a condition to collect carbon nanostructures. It should be noted that during the time of the operation cycle that the collection structure is either removed from production system 102 or in the loaded initial position shown in FIG. 2, the reactant liquid held in reaction chamber 106 is preferably maintained in the desired reactant condition. Maintenance of the reactant liquid in the desired condition during the injection of carbon-bearing feedstock as described below corresponds to the step shown at process block 401 in FIG. 4.

With the air purged from loading chamber 109, insulating door 204 may be opened and manipulating structure 210 lowered to position collection structure 207 in the position shown in FIG. 3. In this lowermost position, shown in FIG. 3, the surfaces associated with collection structure 207 provide collection surfaces in collection chamber 108 on which carbon nanostructures may collect according to the invention. This provision of collection surfaces occasioned by placing collection structure 207 in the position shown in FIG. 3 corresponds to the step shown at 402 in FIG. 4. In this lowermost position, insulating plate 208 fits loosely over the opening for insulating door 204. This loose fit over the opening for insulating door 204 allows purge gas and other gasses to flow up from collection chamber 108 into loading chamber 109 and ultimately exit production system 102 as indicated by arrow 214.

Once production system 102 is in the position shown in FIG. 3, purge gas alone may still be injected into reaction chamber 106 for a period of time to allow the collection structure 207 to reach a desired operating temperature for the production and collection of carbon nanostructures according to the invention. Heater elements 202 may be operated to help heat the contents of collection chamber 108, including collection structure 207. When the temperature of collection structure 207 and the temperature in collection chamber 108 have reached the desired levels, feedstock or feedstock and purging gas may be injected into reaction chamber 106 as shown at arrow 212 in FIG. 3. According to the invention, carbon ions containing one or two carbon atoms are liberated from the feedstock by reaction with the reactant liquid in reaction chamber 106. This injection of feedstock and production of carbon ions corresponds to the process step shown at block 403 in FIG. 4. These carbon ions rise quickly through the reactant liquid and traverse the reactive liquid surface 105 to flow into collection chamber 108 in accordance with the process step shown at block 404 in FIG. 4. Ultimately, the carbon ions bond together to produce the desired nano structured carbon thermal target material and collect on surfaces in collection chamber 108, and particularly surfaces associated with collection structure 207. This collection of carbon nanostructures corresponds to the process step shown at block 405 in FIG. 4. It should be noted that other materials released from the feedstock molecules, such as hydrogen in the case of an acetylene feedstock, are able to rise up through collection chamber 108, pass around plate 208 in the position shown in FIG. 3, together with the argon purge gas and eventually exit loading chamber 109. This venting as indicated by arrow 214 in FIG. 3 is preferably accomplished through the pressure relief valve 110 shown in FIG. 1. The hydrogen gas venting through relief valve 110 in FIG. 1 may be collected as a byproduct of the carbon nanosphere production process.

After a desired collection period in which feedstock is injected into reaction chamber 106 with production system 102 in the position shown in FIG. 3, the feedstock flow is terminated so that only purge gas continues to flow into reaction chamber 106. Manipulating structure 210 is then used to raise collection structure 207 up to the position shown in FIG. 2. At this point, insulating door 204 may be closed to the position shown in FIG. 2 and collection structure 207 may be allowed to cool as necessary to allow the structure to be removed from loading chamber 109. To remove the collection structure 207, the airlock door (not shown) associated with loading chamber 109 is opened and the collection structure 207 is removed as facilitated by the connection to manipulating arrangement 210. Collected carbon nanostructures on the surfaces of collection structure 207 may then be brushed or scraped off onto a suitable surface and then moved to suitable containers. This removal of carbon nanostructures corresponds to the process step shown at block 406 in FIG. 4. Collection structure 207 may then be readied for another cycle of operation. In one preferred process, the surfaces of collection structure 207 are particle blasted to prepare the surfaces for the next operation cycle.

Figure 5:
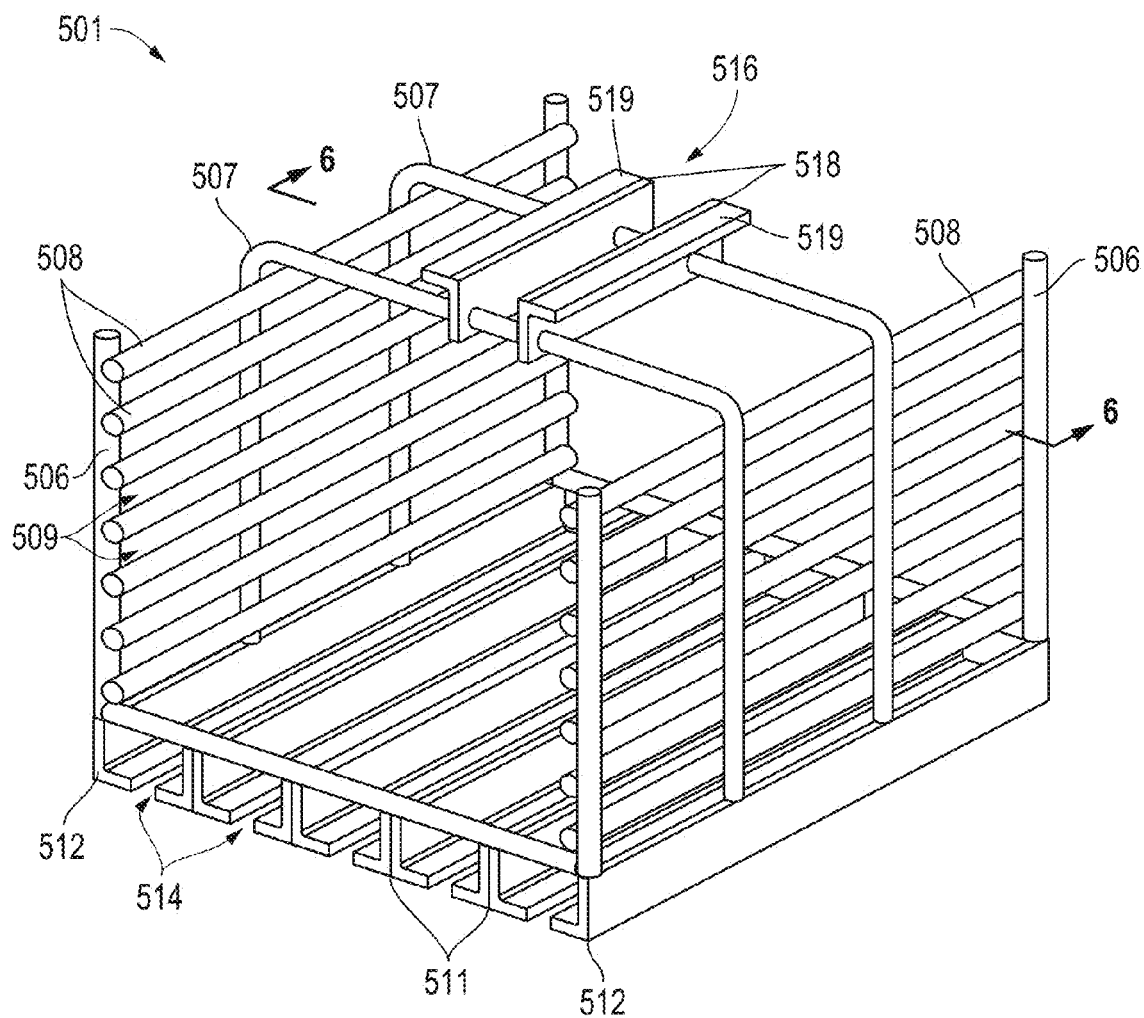
FIG. 5 is an isometric view of a rack used in one preferred collection structure for carbon nanostructures.
Figure 6:
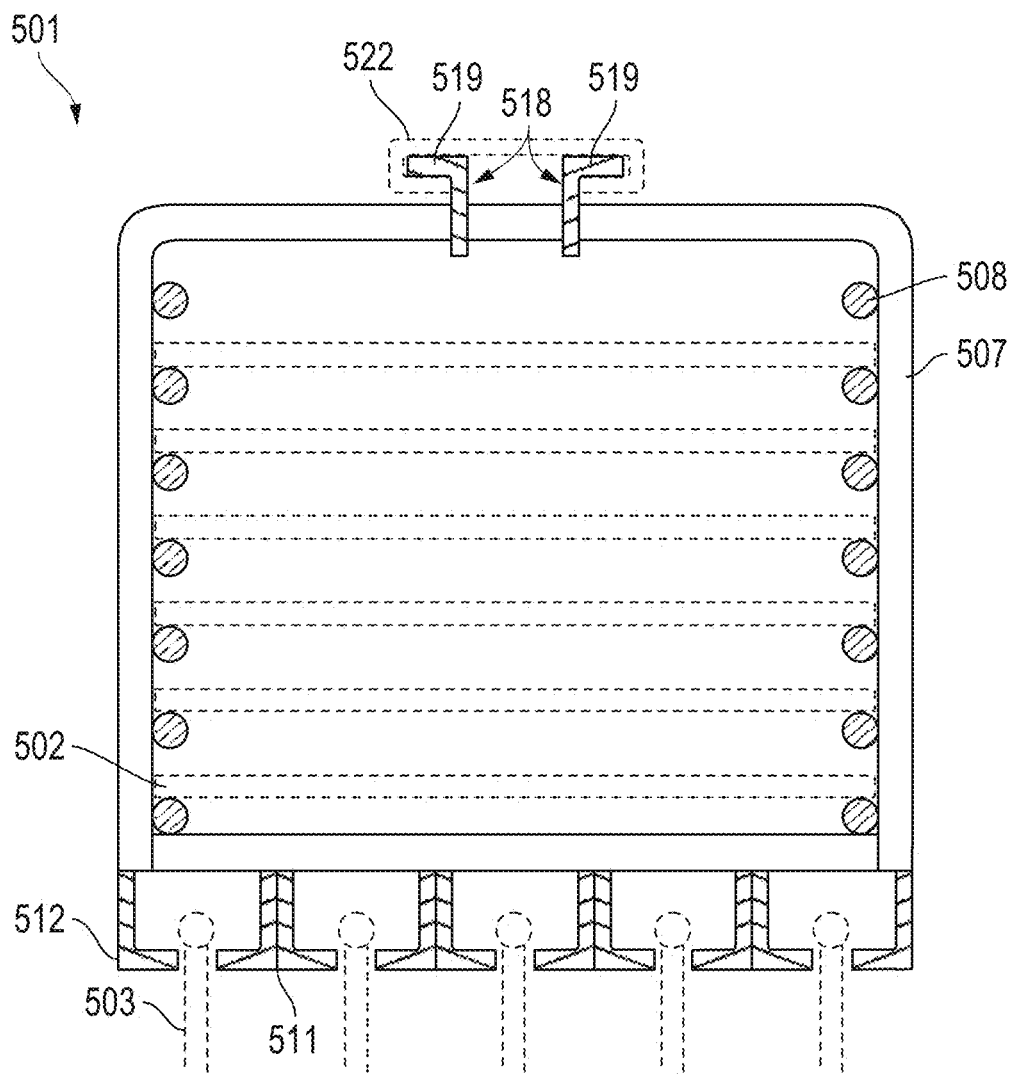
FIG. 6 is a view in section taken along line 6-6 in FIG. 5, and showing collection plates loaded into the rack in phantom lines.

FIGS. 5 and 6 show a rack 501 that may be used as a portion of the collection structure 207 described in connection with FIGS. 2 and 3. This preferred rack 501 supports a number of collection plates which provide the primary collection surfaces for collecting carbon nanostructures that may be employed as thermal targets according to the invention. In order to more clearly show the rack structure, the isometric view of FIG. 5 shows only rack 501 without the collection plates. However, the section view of FIG. 6 shows the plates 502 and 503 in phantom lines as they would be received on rack 501.

Rack 501 includes four U-shaped members, two upwardly facing U-shaped members 506 with one at either end of the structure, and two downwardly facing U-shaped members 507 spaced apart in a center portion of the rack. A series of rods 508 are connected to these U-shaped members 506 and 507 with the rods spaced apart to providing a series of channels 509 for receiving collection plates 502 shown in FIG. 6. The particular rack 501 shown in FIGS. 5 and 6 includes seven rods 508 on each lateral side of the collection structure producing six separate channels 509 which may each receive a collection plate 502. At the bottom of rack 501 are located a series of spaced apart inverted T-shaped structures 511 and angle members 512 which together form five slots 514 for receiving additional collection plates 503. As indicated in FIG. 6, channels 509 hold collection plates 502 in a horizontal orientation while the slots 514 at the bottom of rack 501 support collection plates 503 in a vertical orientation.

Rack 501 also includes an arrangement for enabling the rack to be removably suspended from the manipulating structure 210 shown in FIGS. 2 and 3. The illustrated connecting arrangement 516 includes two angle members 518 which are connected to the two downwardly opening U-shaped members 507 of rack 501. The outwardly facing upper portions 519 of these angle members 518 may be slidably received in a slot mounted at the bottom of manipulating structure 210. FIG. 6 shows this receiving slot structure 522 in phantom lines. In this arrangement, rack 501 may be loaded into the production system 102 shown in FIGS. 2 and 3 simply by opening the airlock door (not shown) associated with loading chamber 109 and inserting the outwardly extending portions 519 of angle members 518 into the slot formed in slot structure 522 located at the bottom of manipulating structure 210. Conversely the collection structure 207 may be removed simply by sliding the upper portions 519 of angle members 518 off of the receiving slot structure 522 and pulling the collection structure through the open airlock door associated with loading chamber 109 (but not shown in the figures).

Methods of producing nanostructured carbon thermal target material according to the invention and the particular carbon nanostructures produced by such methods may be described further in connection with the following examples. Each of these examples used a test apparatus as described above in connection with FIGS. 1 through 3 and a collection structure rack as described in FIGS. 5 and 6. Thus, the various elements of the test apparatus described below will retain the same reference numbers used for the corresponding elements of the structures shown in FIGS. 1 through 3, 5 and 6. In the test apparatus used for these examples, collection chamber 108 comprised a rectangular chamber having internal dimensions of approximately seventeen (17) inches high, fifteen (15) inches wide, and fifteen (15) inches deep. Three rows of heater elements 202 were included against three walls of the collection chamber generally in the position shown in FIGS. 2 and 3. Reaction chamber 106 in the test apparatus had internal dimensions of approximately twenty-five (25) inches high, fifteen (15) inches wide, and fifteen (15) inches deep. Substantially pure aluminum (99% aluminum by mass composition) at a temperature of approximately 1650° F. (1642° F. to 1655° F.) was maintained in the reaction chamber approximately eighteen (18) inches deep. The feedstock material and purge gas were injected into the reaction chamber at approximately seventeen (17) inches below the surface of the liquid aluminum into a tunnel structure 201 as described above in FIGS. 2 and 3. The outlet end or lip of tunnel structure 201 was positioned generally in the center of the reaction chamber approximately sixteen (16) inches below the surface 105 of the liquid aluminum. In each of the examples, the collection plates 502 (and 503 for Example 1 below) shown in FIG. 6 comprise plates of 304 stainless steel approximately three-sixteenths (3/16) of an inch thick. Each of the horizontally arranged plates 502 was ten and a half (10.5) inches wide, and eleven (11) inches deep, while the vertically oriented plates 503 (used only in Example 1) were approximately five (5) inches high and eleven (11) inches deep. The rack 501 itself as shown in FIGS. 5 and 6 was approximately sixteen (16) inches high, thirteen (13) inches wide, and thirteen (13) inches deep. This arrangement left a clearance of approximately 1 inch between rack 501 and the inner wall of collection chamber 108. Other operating parameters for the test apparatus will be described in connection with the respective example.

Example 1

In one test of the apparatus described above, rack 501 was loaded with six horizontal collection plates 502 spaced approximately one-half inch apart and five vertical collection plates 503 spaced approximately one and one-half (1.5) inch apart. The collection structure 207 made up of rack 501 and loaded collection plates 502 and 503 was then placed into loading chamber 109 suspended on manipulating structure 210 as described above in connection with FIG. 6. The airlock door associated with loading chamber 109 was then closed and the continuously injected argon gas allowed to purge the loading chamber of air that entered as the airlock door was open. After purging loading chamber 109 of air, insulating door 204 was opened and manipulating structure 210 was used to lower collection structure 207 from the position shown in FIG. 2 to the position shown in FIG. 3. In this lowered position, with collection structure 207 residing in collection chamber 108, the lowermost ends of the vertically oriented collection plates 503, resided approximately two (2) inches above the surface 105 of the liquid aluminum reactant liquid. From this point in the collection test, only argon was still continuously injected into the reactant liquid and heater elements 202 were operated to increase the temperature of the collection structure 207 to approximately 1400° F. Once this collection surface temperature was reached, commercial grade acetylene at room temperature of approximately 70° F. was injected into the reactant liquid at a rate of approximately two (2) liters per minute along with the argon gas also at approximately two (2) liters per minute. This injection of argon gas and acetylene was continued for a period of approximately two (2) hours until approximately 133 grams of carbon from the acetylene had been injected. The injection of the acetylene was then stopped leaving the continuous stream of argon gas at approximately two (2) liters per minute.

Once the injection of the acetylene was stopped, manipulating structure 210 was used to raise collection structure 207 up into the position shown in FIG. 2, with the collection structure residing in loading chamber 109, and insulating door 204 was closed. Collection structure 207 was then allowed to cool to approximately 212° F. at which point the airlock door associated with loading chamber 109 was opened, and the collection structure was removed to an aluminum foil-covered table top. The vertical plates 503 were removed from rack 501 prior to placing the rack on the foil-covered table. A shiny and powdery appearing, black material was observed on the surfaces of all of the collection plates 502 and 503 and on the surfaces of rack 501 itself. Plastic foam brushes were used to brush off the black material onto the aluminum foil and then the black material was placed into glass sample containers. This test and black material recovery procedure yielded approximately sixty (60) or more grams of the black material.

Figure 7:
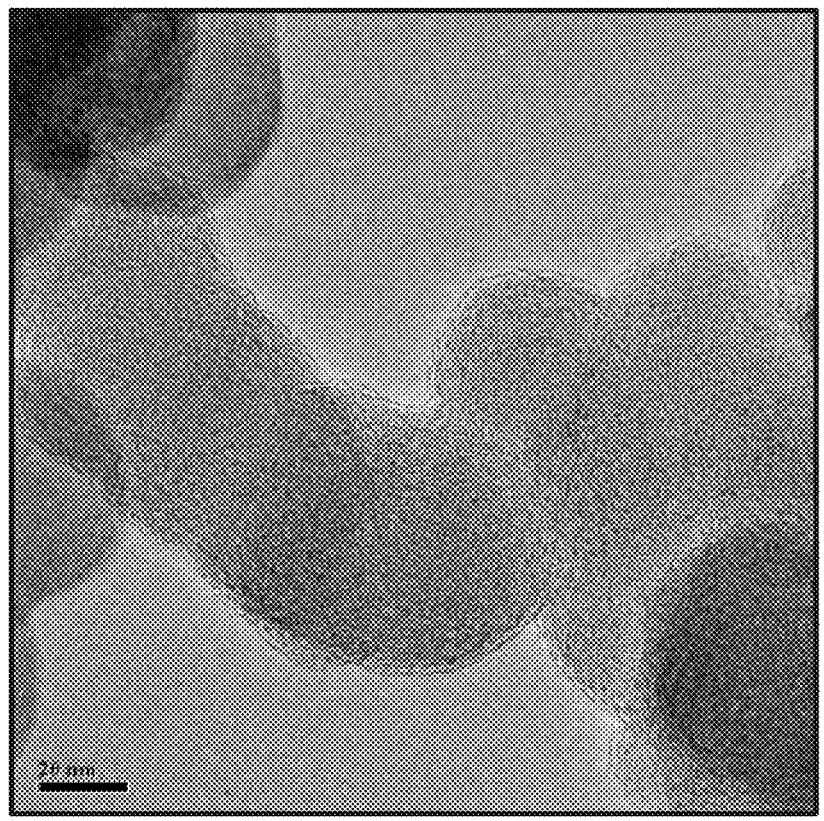
FIG. 7 is a transmission electron microscope image of a sample of material collected in Example 1.
Figure 8:
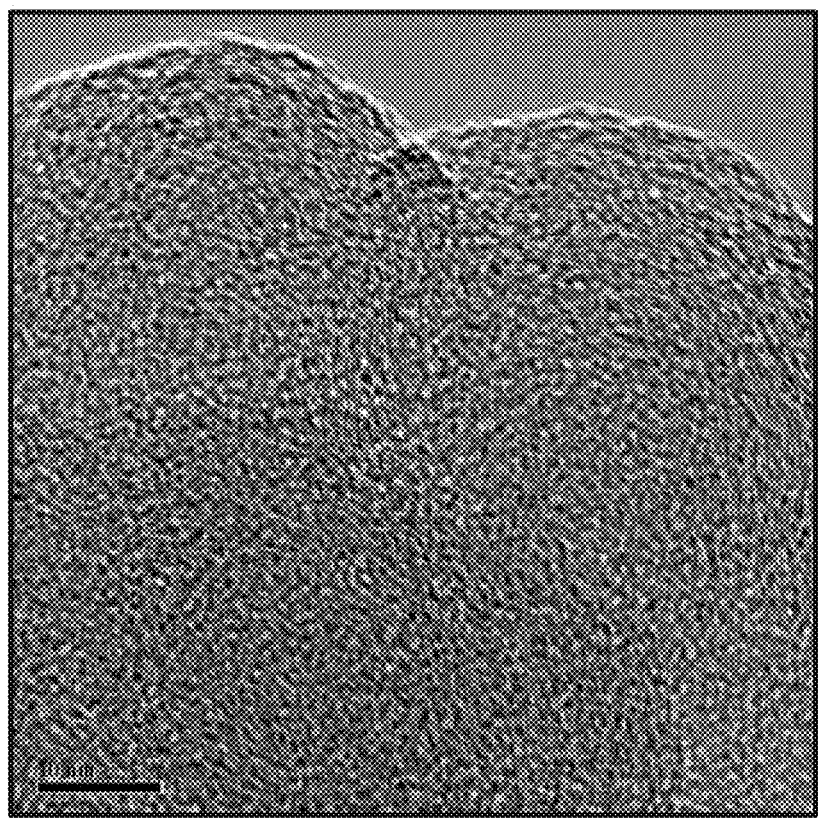
FIG. 8 is a transmission electron microscope image of a sample of material collected in Example 1, but at a higher level of magnification as compared to the image shown in FIG. 7.
Figure 9:
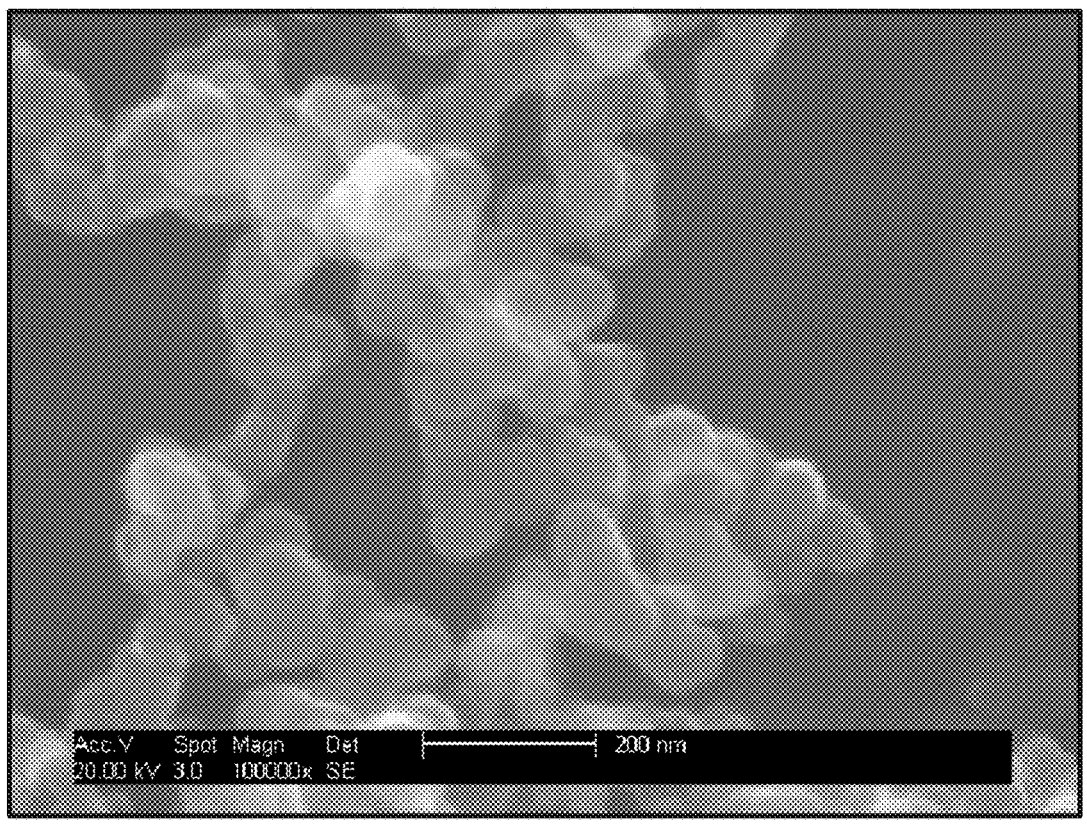
FIG. 9 is a scanning electron microscope image of a sample of material collected in Example 1.
Figure 10:
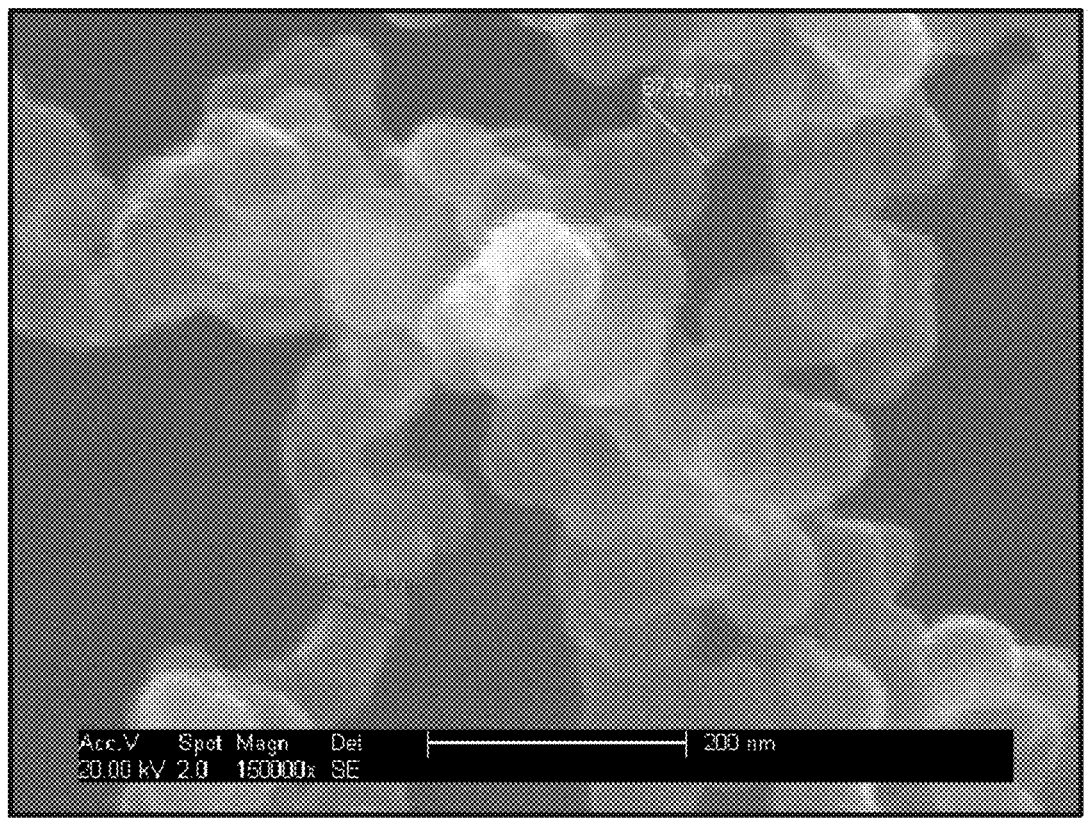
FIG. 10 is another scanning electron microscope image of a sample of material collected in Example 1 including dimension markings for some of the spherical structures.

The black material collected in these sample containers was later examined with a transmission electron microscope (TEM) and scanning electron microscope (SEM). FIGS. 7 and 8 are TEM images of the collected black material. These images show that the black material collected as described above is made up almost exclusively of spherical structures. The TEM image shown in FIG. 8 shows that the spherical structures are highly ordered consistently across the surface of each sphere, and that the spheres appear to be composed of a series of concentric strings of carbon material. These concentric strings appear consistent throughout a significant portion of the surface of the respective spherical structure, that is, throughout 50% or more of the respective sphere surface visible in FIG. 8. FIGS. 9 and 10 are SEM images of this same material collected as described above. These SEM images were taken from the same sample of the collected material which produced the TEM images of FIGS. 7 and 8. The SEM images confirm the uniform spherical structures making up the material. The spherical carbon nano structures included in the sample material were as small as approximately sixty-two (62) nanometers in diameter as shown in FIG. 10. Energy dispersive spectroscopy (EDS) at two locations in material from this sample having the structure shown in FIGS. 7 through 10 showed that the material was made up largely of carbon with only a small percentage of oxygen. Specifically, one EDS result indicated that the spherical material was 94.37% carbon by mass composition, and 5.03% oxygen by mass composition. The second EDS result indicated the spherical material was 96.43% carbon mass composition and 3.57% oxygen by mass composition. It is believed that the oxygen atoms indicated in the EDS results were not incorporated in the spherical structures themselves, but were extraneous atoms included in among the spherical structures.

The collection process described above was performed seven times in one series of tests. The following table shows the temperatures measured in the collection structure 207 at the start of the acetylene injection and at the end of the acetylene injection. TEM and SEM analyses of samples taken from all of these seven test operation cycles showed results similar to those shown in FIGS. 7 through 10.

TABLE 1

| Starting Temperature (° F.) | Ending Temperature (° F.) |
| --- | --- |
| 1394 | 1543 |
| 1378 | 1526 |
| 1375 | 1441 |
| 1521 | 1616 |
| 1415 | 1569 |
| 1370 | 1416 |
| 1527 | 1608 |

The reaction of the acetylene with the aluminum reactant liquid in this example is believed to produce two different carbon ions, together with hydrogen atoms released from the original feedstock molecules. It is believed that the reaction in the reactant liquid releases one double-bonded C2 carbon ion and two hydrogen atoms from each acetylene molecule. As the carbon ions and hydrogen atoms leave the bath, it is believed that the carbon ions quickly bond to form the ring structures and interconnected ring structures described below in connection with FIGS. 15 and 16. However, the hydrogen atoms are much too energetic to bond back to the carbon and are left to bond with other hydrogen atoms to form diatomic hydrogen which exits the system with the purge gas.

It should also be noted that tests similar to those set out in Example 1 were conducted with various metal catalysts included on the collection surfaces. Iron, cobalt, and nickel catalysts were used in different tests with the acetylene feedstock. In these tests, with the collection surfaces starting at a temperature of around 1450° F., carbon nanofibers were collected on the collection surfaces rather than the carbon nanospheres shown in FIGS. 7 through 10.

Example 2

Figure 11:
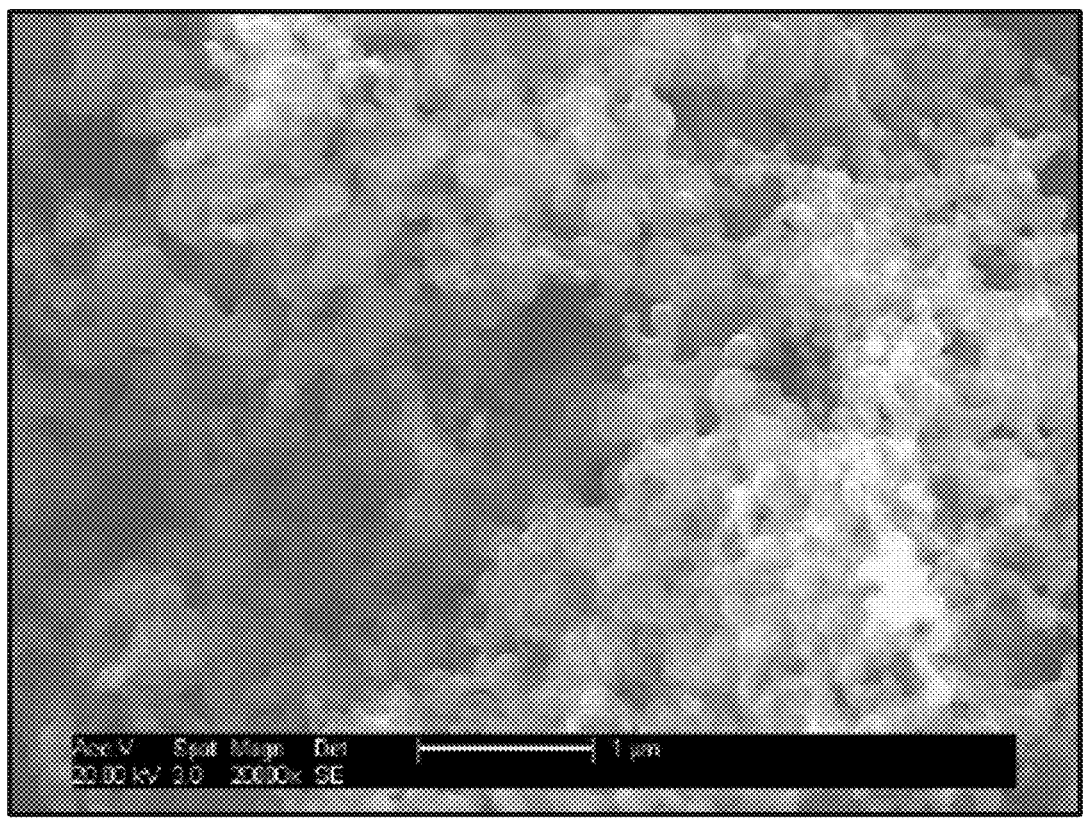
FIG. 11 is a scanning electron microscope image of a sample of material collected in Example 2.
Figure 12:
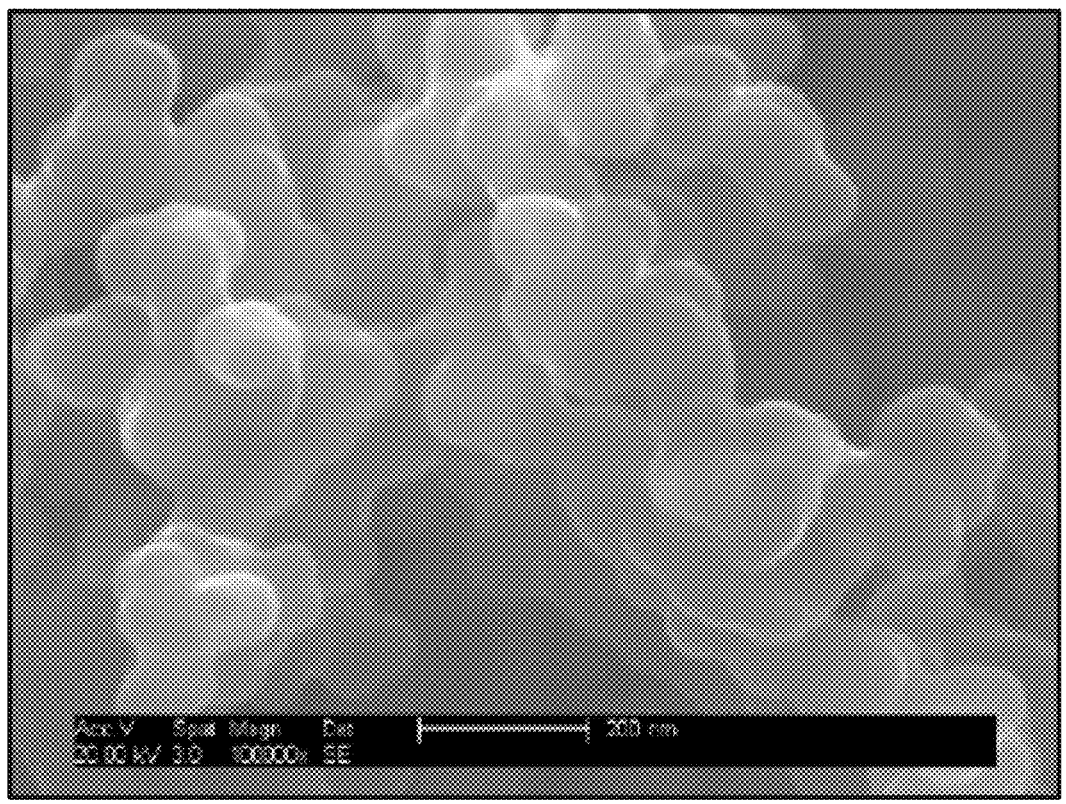
FIG. 12 is another scanning electron microscope image of a sample of material collected in Example 2.
Figure 13:
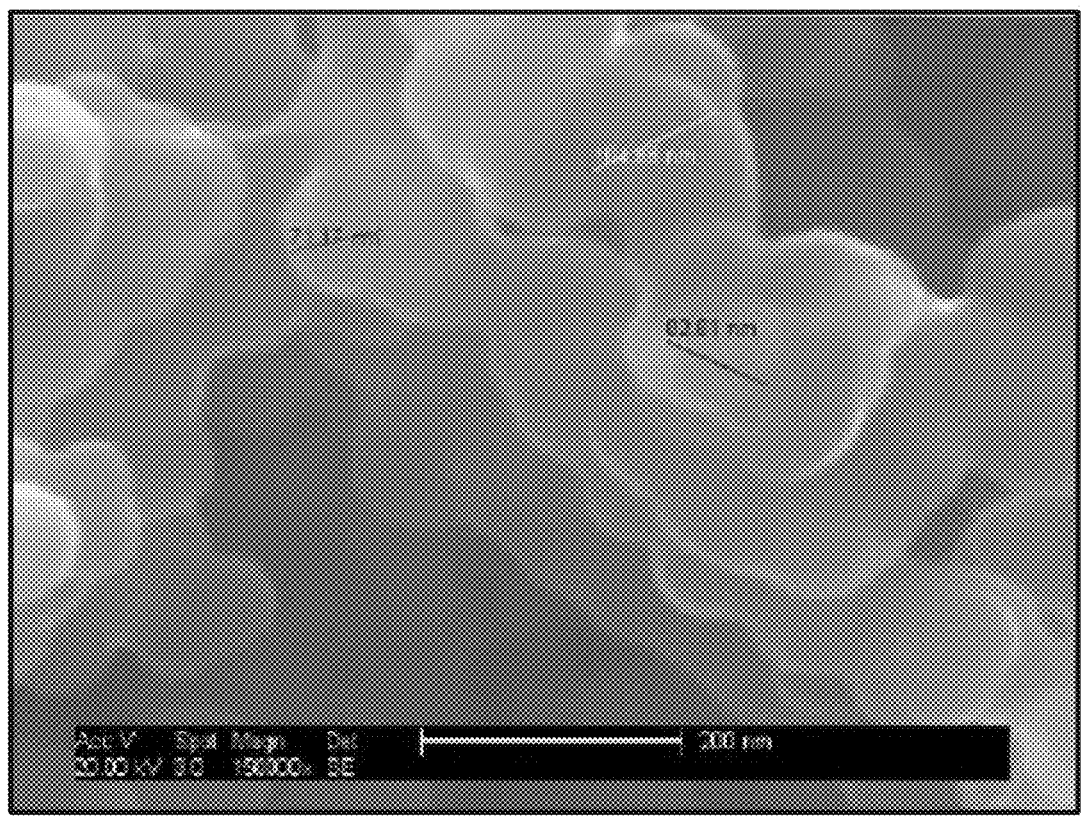
FIG. 13 is another scanning electron microscope image of a sample of material collected in Example 2 including dimension markings for some of the spherical structures.

The same procedure described in Example 1 above was conducted in an additional series of tests each using a lower initial temperature of collection structure 207 prior to starting the injection of the acetylene, and using only horizontal collection plates 502. In these collection procedures, once collection structure 207 was in the position shown in FIG. 3, heater elements 202 were not activated and the acetylene was injected immediately, prior to any significant heating of the collection structure. In these tests, the starting temperature of collection structure 207 was approximately 100° F., and the ending temperature was approximately 590° F. Also, for these tests, the flow of acetylene was increased to seven (7) liters per minute for the injection period of two (2) hours. FIGS. 11-13 show SEM images of material collected from one of these tests. As shown in the SEM images, these tests also produced generally spherical carbon nanostructures with some as small as approximately seventy-one (71) nanometers in diameter. An EDS result for the spherical material from the same sample as the spherical material shown in FIGS. 11-13 indicates the material includes 99.29% carbon by mass composition and 00.71% oxygen by mass composition.

Although the above-described tests were performed with a rack and plate type collection structure 207 described above, it is believed that other types of collection arrangements may be employed for collecting carbon nanostructures which form above the level 105 of the reactant liquid in reaction chamber 106 shown in FIG. 1. In particular, rather than employing a rack and plate type collection structure 207 as described above, the material exiting the reactant liquid may be drawn off by vacuum or otherwise through one or more conduits (not shown) having a respective inlet positioned in collection chamber 108. The entire collection chamber 108 may in fact represent the inlet to a collection conduit through which the carbon and all gasses pass to exit the system.

Figure 14:
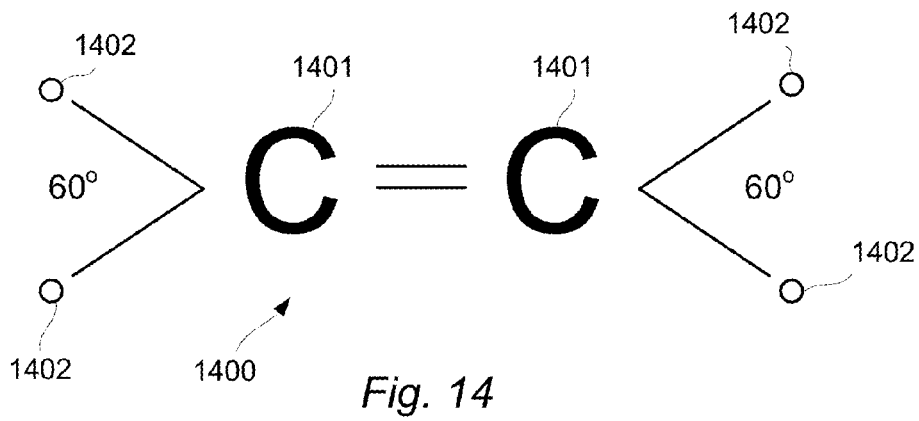
FIG. 14 is a diagrammatic representation showing the chemical structure of a double-bonded carbon C2 ion (acetylide ion) liberated from the acetylene feedstock to produce spherical carbon nano structures.

FIG. 14 shows a diagrammatic representation of a carbon ion 1400 that is believed to be isolated from acetylene in the reactant liquid in the process described above. This carbon ion 1400 includes the two double-bonded carbon atoms 1401 from the acetylene molecule (not shown) with four unfilled bond sites, that is, four unbound electrons 1402, two at each end of the structure. As indicated in FIG. 14, a bond may form within a cone of 60 degrees on each end of carbon ion 1400. This carbon ion 1400 is believed to be liberated in the reaction of acetylene and liquid reactant because the energy of the reactant liquid (e.g. liquid aluminum at 1650° F.) is only sufficient to break the carbon-hydrogen bonds in the acetylene molecules and the sigma bond in the acetylene triple-bonded molecules. Based on this carbon ion structure 1400, it is believed that the material produced according to the present invention and the above-described tests includes the atomic structure made up of these carbon ion structures bonded together with single carbon bonds.

Figure 15:
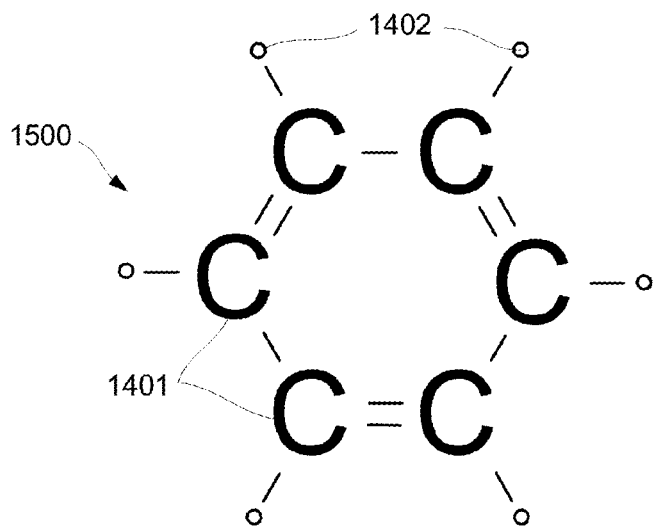
FIG. 15 is a diagrammatic representation showing the basic carbon ring structure within a spherical carbon nano structure that may be used in a thermal target material according to the present invention.
Figure 16:
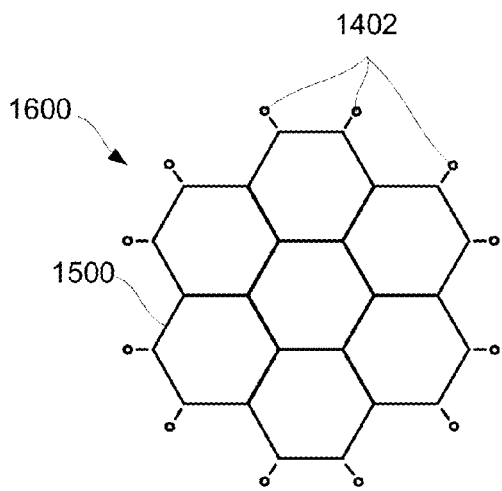
FIG. 16 is a diagrammatic representation showing a group of the carbon ring structures shown in FIG. 15, bonded together to form a basic building block for a spherical carbon nano structure that may be used as a thermal target material according to the present invention.

The potential atomic structures making up the spherical carbon nanostructures are shown diagrammatically in FIG. 15 or 16. As indicated in FIG. 15, it is believed that the spherical carbon nanostructures are made up of combinations of carbon atoms 1401 having alternating double and single bonds. The carbon atoms 1401 are arranged in rings as indicated in the structure 1500 shown in FIG. 15. It will be noted that ring structure 1500 includes one unbound electron 1402 projecting from each carbon atom 1401. Each of these electrons 1402 in FIG. 15 represents a site for bonding with another carbon ion 1400 to ultimately produce an additional joined ring structure. The configuration of carbon atoms 1401 shown in FIG. 15 may interconnect due to the unbound electrons 1402 on each carbon atom to form structure 1600 in FIG. 16. This structure 1600 is made up of seven interconnected ring structures 1500 and leaves twelve unbound electrons 1402 at the periphery of the structure. It is believed that seven-ring structures such as structure 1600 form the basic building blocks of the spherical carbon nano structures. It is also believed that the unbound electrons 1402 throughout the spherical carbon nanostructures are responsible for the unique microwave absorption properties of the carbon material.

Description of Preferred Thermal Target Materials

A preferred thermal target material according to the present invention includes a low-hydrogen, nanostructured carbon material in a suitable carrier fluid. The nanostructured carbon material is preferably arranged in a spherical shape or interconnected clusters of spherical shapes, with individual sphere diameters ranging from 15 nm to 110 nm. However, other sizes of carbon nanospheres may be suitable for use in a thermal target material according to the invention as may other forms of nanostructured carbon provided the carbon structures include large numbers of unbound electrons similar to the spherical carbon nanostructures described above. For example, the material may be carbon nanofibers, carbon nanoropes, and carbon nanotubes formed in a reactant liquid process as described above so that any hydrogen eluding from the reactant liquid with the carbon ions is unable to bond back to the carbon, thereby leaving unbound electrons in the resulting carbon structures. Such low-hydrogen carbon nanotubes may be single or multi-walled nanotubes. Amorphous carbon may also make a suitable material for inclusion in a thermal target material according to the invention provided the carbon produces the desired microwave absorption properties which are believed to result from the absence of hydrogen in the carbon and the consequent unbound electrons.

The nanostructured carbon employed in thermal target material according to the present invention has been found to efficiently absorb incident microwave radiation and then emit heat energy. Testing of the spherical nanostructured carbon produced according to the process described above has found that spherical nanostructured carbon material suspended in water at a concentration 0.0277 moles of the carbon material per 100 milliliters of water, when subjected to microwave radiation at 2.45 GHz in a conventional 1500 watt microwave oven, reaches the boiling temperature of the water in approximately 52.3% of the time required for 100 milliliters of plain water to reach the boiling temperature when subjected to the same microwave radiation. The carbon material was made up of clusters of individual spheres between approximately 60 nm to 105 nm in diameter, and these clusters were suspended in the water. As will be discussed further below in connection with the present treatment methods, the heat energy radiated from the thermal target material in response to the incident microwave radiation is much higher than the heat energy released in the biological tissues by direct absorption of the microwave energy. The difference between the heat released by microwave absorption in the thermal target material and the heat released by direct microwave absorption in the biological tissue is such that the desired heat may be produced from the thermal target material well before damaging heat is produced from direct absorption of microwaves in the biological tissue.

The nanostructured, low-hydrogen carbon material is preferably combined with a suitable carrier fluid to make a suitable thermal target material that may be readily introduced at the desired points within a patient's body. For example, the carbon material may be dispersed with a suitable toxicologically acceptable dispersing agent in water or saline solution. The dispersing agent may comprise a suitable surfactant. The carbon bearing liquid may also be gelled with a suitable toxicologically acceptable gelling agent to increase the viscosity in the liquid and help suspend the carbon particles. Suitable gelling or viscosity enhancing agents include gelatin, agar, and cornstarch for example The amount of nanostructured carbon material in the overall thermal target material must be sufficient to produce the desired heat for the therapeutic application without requiring excessive microwave radiation applied to the biological tissue to be treated and nearby tissue. An excessive amount of microwave radiation is that amount that would cause undesirable heating by direct absorption in the biological tissue, that is, heating that would kill or damage the biological tissue. It is believed from the microwave absorption properties of the nanostructured carbon material that as little as $1.18 \times 10^{-6}$ grams of the nanostructured carbon material may be an effective amount for hyperthermally ablating an adjacent biological cell from heat energy released from the carbon material as a consequence of the absorption of microwave radiation by the carbon material.

Methods of Employing Thermal Target Materials

Figure 17:
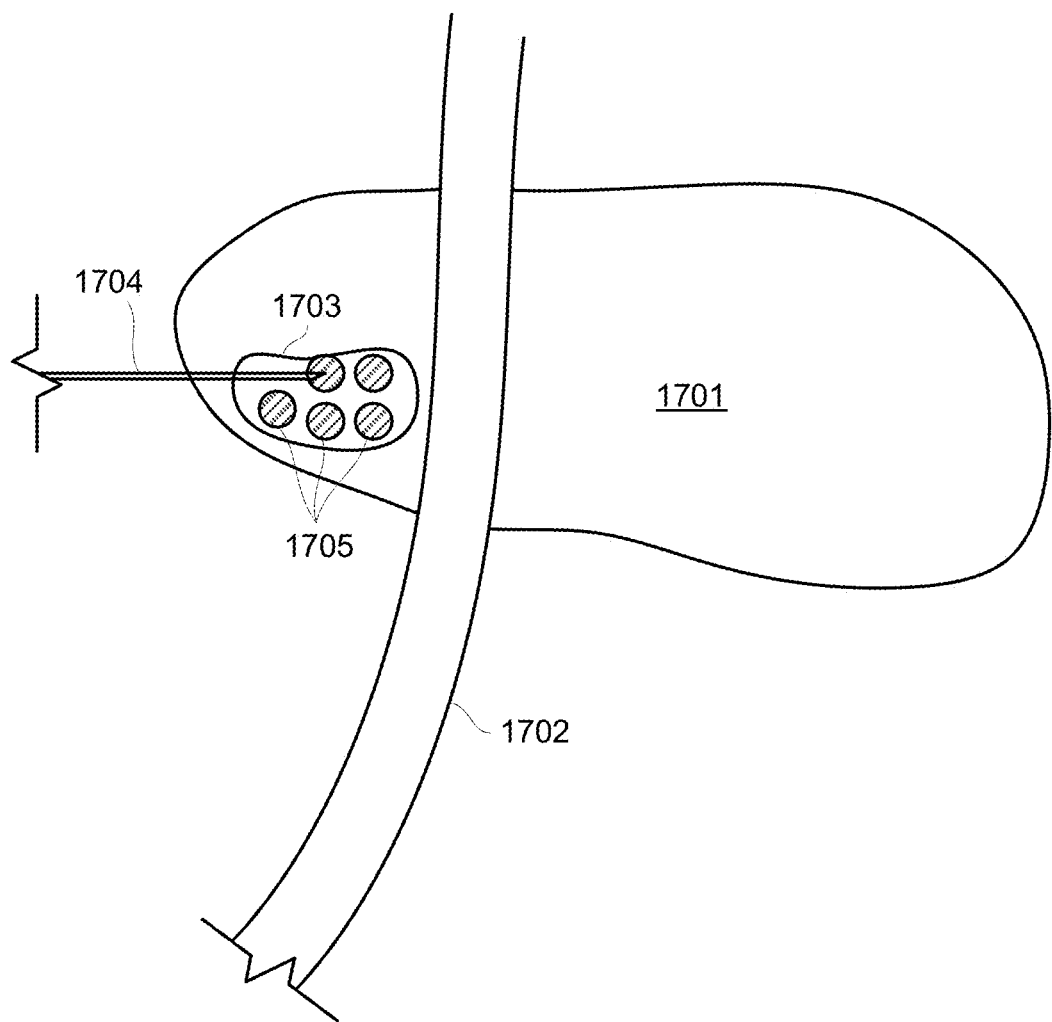
FIG. 17 is a diagrammatic representation showing biological tissue to be treated and the placement of thermal target material with respect to the biological tissue to be treated.

FIGS. 17 through 20 may be used to describe treatment methods according to one preferred form of the invention for treating diseased tissue. FIG. 17 shows a representation of the prostate gland 1701, urethra 1702, and a cancerous tumor 1703 within the prostate. In the diagrammatic representation of FIG. 17, tumor 1703 is located generally in the anterior portion of the prostate gland 1701 forward of urethra 1702. A treatment material and method according to the present invention may be applied to hyperthermally ablate the cells of tumor 1703 while leaving nearby normal cells of the prostate 1701 and urethra 1702 intact and undamaged.

A method according to the present invention includes positioning a thermal target material as described above at a treatment site adjacent to biological tissue to be treated. In the example of FIG. 17 the thermal target material comprises particles of nano structured, low-hydrogen carbon dispersed within a carrier fluid such as water, and is placed at the desired treatment site within tumor 1703 by injection through a suitable injection needle 1704. FIG. 17 shows multiple locations at which thermal target material has already been placed via injection conduit 1704, and these locations are labeled 1705 in the drawing. The position of injection conduit 1704 shown in FIG. 17 is shown only for purposes of example is not limiting. It is expected that the manner in which a thermal target material is placed according to the invention will be highly dependent upon the specific location of the tissue to be treated and the therapeutic object of the treatment. Where an injection conduit such as conduit 1704 is used to inject a thermal target material according to the invention, ultrasonic imaging may be used to help guide the practitioner in placing the injection conduit to inject the thermal target material at the desired locations. Other thermal target material placement techniques may employ a suitable device designed to be inserted through a passageway of the body. For example, it may be possible to inject the thermal target material into tumor 1703 shown in FIG. 17 through a device that is inserted through urethra 1702. In yet other forms of the invention, thermal target material may include no carrier fluid and may be placed by a surgeon through a suitable incision in the patient. Instruments such as endoscopes may be used to minimize the incision required to reach the desired treatment site and place the thermal target material at the treatment site. In yet other forms of the invention, a thermal target material may include an agent that has an affinity for cells to be treated. Such an agent may be applied to the nanostructured carbon particles and used to cause the nanostructured carbon particles in the thermal treatment material to be attached to the cells to be treated, or perhaps even taken up within the cells to be treated. In this respect, target specific ligands of the type described in U.S. Pat. No. 7,074,175 may be used in conjunction with the nanostructured carbon particles to position the nanostructured carbon particles adjacent to the biological cells to be treated. The entire content of U.S. Pat. No. 7,074,175 is incorporated herein by this reference.

Regardless of the specific manner in which the thermal target material is positioned at the treatment site, a sufficient amount of the thermal target material is positioned to provide the desired treatment area with the desired amount of heat energy when the thermal target material, and particularly the nanostructured carbon material included in the thermal target material, is subjected to microwave radiation. An effective amount of the thermal target material is an amount that provides the desired therapeutic heating to the desired area, that is, the desired biological tissue, without requiring excessive exposure to the microwave radiation. Excessive exposure to microwave radiation is that exposure which produces undesirable heating in the biological tissue by direct absorption of the microwave radiation in the biological tissue. Limitations on the amount of microwave radiation that may be applied in a treatment according to the present invention, and effective treatment range for particles of the nanostructured carbon material will be described further below with reference to FIGS. 19 and 20.

Referring again to the example of FIG. 17 it is assumed that the thermal target material is injected at multiple points 1705 within tumor 1703 to be treated. The number of points at which a thermal target material may be placed in a treatment method according to the invention will depend on the size of the area to treated, the dispersive properties of the thermal target material, and the effective treatment range of the nanostructured carbon for the given application. It will be appreciated that particularly where the thermal target material includes a liquid carrier, the material will disperse somewhat within the biological tissue upon injection. The round (spherical) dispersal pattern shown in FIG. 17 is shown only for purposes of illustration and may not reflect an actual dispersal pattern within a biological tissue. The manner in which thermal target material disperses within a mass of biological tissue will depend upon the nature of the thermal target material, particularly the liquid in which the carbon may be carried, and the nature of the tissue into which the thermal target material is injected or otherwise placed.

The positioning of a thermal target material according to the present invention will also depend upon the nature of the treatment to be provided. Tumor 1703 shown in FIG. 17 is sufficiently large to require multiple injection points assuming the spherical dispersion pattern shown in figure. However, in some applications the material to be treated may not be sufficiently large to require multiple injection points or application points for the thermal target material. Also, the applicants believe that the thermal target material may, in some cases, be placed around a mass of biological tissue to be treated rather than within the mass of biological tissue.

Figure 18:
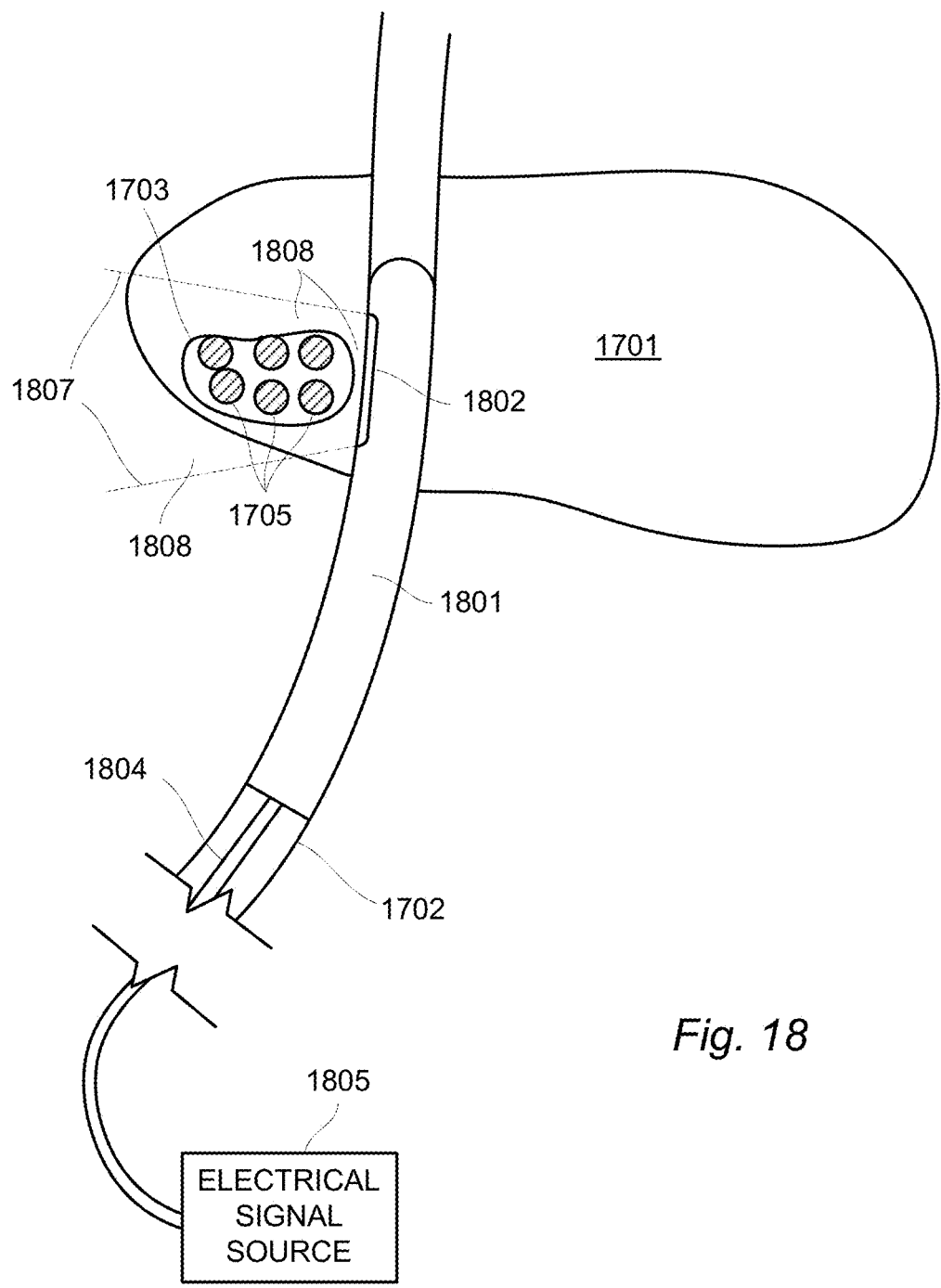
FIG. 18 is a diagrammatic representation similar to FIG. 17 but showing the position of a microwave source to apply microwave radiation to the thermal target material.

FIG. 18 shows tumor 1703 and after all of the desired thermal target material has been placed at locations 1705, and injection device 1704 has been withdrawn. FIG. 18 also shows a microwave emitting antenna assembly 1801 that has been inserted into the patient's urethra 1702 to a location in which a microwave emitting window 1802 of the antenna assembly is positioned so as to direct microwave radiation toward tumor 1703 and thermal target material locations 1705. Any suitable microwave emitting antenna may be used according to the invention to provide the microwave energy necessary to result in the desired temperature rise locally around the thermal target material locations 1705. A suitable antenna assembly will generally include an antenna (not shown in FIG. 18) contained in some sort of housing. A suitable microwave emitting antenna is shown in U.S. Pat. No. 7,115,126. The antenna shown in U.S. Pat. No. 7,115,126 provides a highly directional beam of microwave radiation from within a natural passageway in the body, and thus may be ideally suited for prostate treatment applications of the type shown in FIGS. 17 and 18. Regardless of the specific structure of antenna assembly 1801 and the antenna included therein, the assembly receives a driving electrical signal through transmission line 1804. Transmission line 1804 is ultimately connected to a suitable signal generating device 1805 that generates the electrical driving signal, which, when applied to the antenna included in antenna assembly 1801, causes the antenna to emit microwave radiation at the desired frequency and power level. With regard to the power level of the microwave radiation emitted from antenna assembly 1801 and the applicability of the antenna assembly shown in U.S. Pat. No. 7,115,126, it should be noted that the antenna assembly described in U.S. Pat. No. 7,115,126 is intended for microwave ablation which will require much higher microwave power levels than the thermal treatment process described and claimed in this application. Thus although the antenna assembly shown in U.S. Pat. No. 7,115,126 may be appropriate for some applications of microwave radiation according to the present invention, it is expected that much lower emitted microwave power levels will be required for applications of treatment methods according to the present invention.

Even with a highly directional antenna such as that shown in FIG. 18 and described in U.S. Pat. No. 7,115,126, it will generally not be possible to limit the microwave radiation to just the thermal target material locations 1705. As shown in FIG. 18, the longitudinal emission pattern 1807 of antenna assembly 1801 is such that the microwave radiation is directed to areas outside of the bounds of tumor 1703 and thermal target material locations 1705. Specifically, microwave radiation emitted in longitudinal emission pattern 1807 passes through nearby biological tissue at various points indicated by reference numeral 1808. These nearby areas beyond the tissue to be treated and thermal target material locations 1705 include areas of tissue above and below tumor 1703 in the orientation of FIG. 18, and areas of tissue located between antenna assembly 1801 and tumor 1703. Since microwave radiation will be emitted from antenna assembly 1801 across some radial arc about the longitudinal axis of the antenna assembly, it is likely that microwave radiation will also be directed both in front and in back of tumor 1703 in the orientation of FIG. 18. However, as will be described further below, the microwave radiation is emitted at a power level and for a period of time such that the direct absorption of the microwave radiation by the biological tissue does not damage the tissue. Rather, the efficiency with which the nano structured carbon material absorbs the incident microwave radiation and emits heat energy is such that the microwave radiation power level and emission time remains at a non-damaging level with respect to all biological tissue that the microwave radiation may encounter in the course of treatment.

As microwave radiation is emitted from antenna assembly 1801 in the direction toward tumor 1703 and the thermal target material locations 1705, a portion of the emitted microwave radiation is absorbed by the nano structured carbon material within the thermal treatment material locations 1705. The absorbed microwave radiation causes a rapid temperature increase in the carbon material and also causes the carbon material to emit infrared radiation. The energy radiated from the carbon material by conduction and by the infrared radiation causes the biological material adjacent to the carbon material to also heat rapidly. This heating from energy radiated from the carbon material is far faster than heating in the biological tissue by direct absorption of the microwave radiation by the tissue. The power level of the microwave radiation emitted from antenna assembly 1801 and the emission time is controlled so that the heat energy radiated from the carbon particles in the thermal target material is sufficient to heat all of the cells of tumor 1703 to the point at which the tumor cells are denatured and killed (typically a temperature at approximately 40° C. to 46° C.). It will be appreciated that some nearby normal cells, that is, cells outside of tumor 1703, may be heated sufficiently to denature the cells, however, the heating is via heat energy radiated by the carbon particles in the thermal target material and not by direct absorption of the microwaves. The power level of the microwave radiation and the time that the microwave radiation is applied, together with careful placement of the thermal target material may be controlled in practice to limit this sort of incidental damage to nearby normal cells, and restrict the damage to the intended abnormal cells.

Although the example of FIGS. 17 and 18 assume that the therapeutic treatment to be applied is a treatment to denature and kill the cells of a biological tissue, the invention is not limited to this application. As discussed above, the placement of thermal target material and application of microwave energy may be used to provide localized heating to enhance biological processes such as healing processes. In these applications of the invention, the effective quantity of microwave energy and effective amounts of thermal target material are those that produce the heating suitable to enhance the biological processes without damaging cells.

It should also be appreciated that although FIG. 18 provides an example where microwave antenna assembly 1801 is positioned through a natural passageway, urethra 1702, other applications of the invention may place a microwave emitting antenna assembly differently. For example, it may be necessary to insert a suitable microwave antenna assembly through an incision in the patient to position the antenna to transmit the desired microwave radiation to the desired thermal treatment target locations. Also, it may be possible in some applications of the invention that the microwave radiation source that is, the microwave emitting antenna assembly may be positioned outside of the patient's body and still provide sufficient microwave energy to the carbon of the thermal target material to produce the desired therapeutic effect without producing damage to cells from incidental absorption of microwave energy in those cells.

Figure 19:
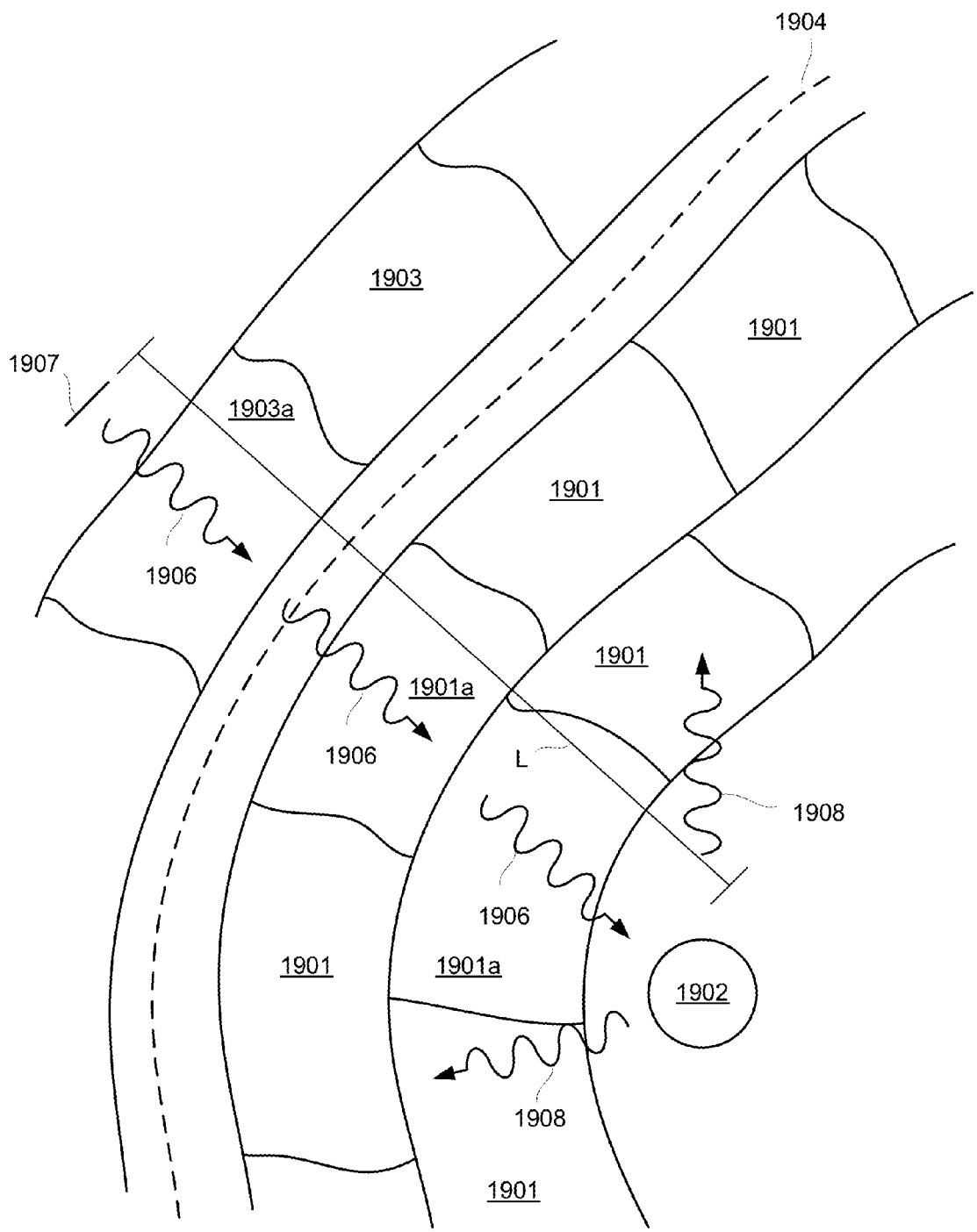
FIG. 19 is a conceptual representation showing the absorption of microwave radiation by carbon molecules in a treatment material and the emission of infrared radiation from the carbon molecules.

FIG. 19 shows a diagrammatic representation of individual biological cells to be treated 1901 and 1901a along with a carbon particle 1902 included in a thermal target material according to the invention and normal cells 1903 and 1903a that are not to be treated. FIG. 19 also shows a fictitious boundary line 1904 between the normal cells 1903 and 1903a, that is, the nearby cells that are not to be treated, and the cells to be treated 1901 and 1901a. It should be noted that FIG. 19 is not to scale and that the biological cells 1901, 1901a, 1903, and 1903a may be on the order of 100 times larger than the size of a particle made up of nanostructured carbon molecules. Also, although FIG. 19 shows simply a single element identified as carbon particle 1902, it will be appreciated that this "particle" may be a single carbon nanostructure in spherical or some other form, or may be a large number of individual carbon nanostructures.

FIG. 19 shows microwave radiation 1906 directed from an antenna assembly surface shown as line 1907. This microwave radiation 1906 is directed toward carbon particle 1902. FIG. 19 also shows infrared radiation 1908 emitted from carbon particle 1902. Heat energy may also be radiated by conduction from carbon particle 1902, although it is believed that the majority of the heating effect produced from the carbon material is from emitted infrared radiation rather than through conduction, that is, the transfer of kinetic energy. In any event, the energy emitted from carbon particle 1902 is believed to be emitted relatively uniformly in all directions from the carbon particle in response to the absorption of microwave radiation 1906.

Microwaves emitted from antenna assembly surface 1907 must traverse a distance L in order to reach carbon particle 1902, and this distance L encompasses both a normal cell 1903a and cells to be treated 1901a. Microwave radiation traversing distance L will be attenuated by absorption in the intermediate cells between the antenna assembly surface 1907 and carbon particle 1902 that is, by cells 1903a and 1901a positioned along the microwave radiation route between the antenna assembly surface 1907 and carbon particle 1902. The microwave radiation adjacent to antenna assembly surface 1907 will thus be at a higher power level than the microwave radiation that ultimately reaches and is absorbed by carbon particle 1902. This absorption of microwave radiation by the intermediate cells sets a maximum distance that the microwaves may penetrate before reaching carbon material 1902. That is, the microwaves emitted from the source antenna must be strong enough so as to have a sufficient power level at carbon particle 1902 to emit the desired amount of heat energy, but low enough so that the microwave radiation absorbed by the intermediate cells, and particularly cells such as 1903a closest to the microwave source do not receive sufficient microwave energy to produce undesirable heating in those cells. However, due to the efficiency at which the carbon particle 1902 absorbs microwave radiation and emits heat energy, it may be possible to place the microwave source antenna at some distance from the treatment site, that is, the location of the thermal target material, and still provide an effective amount of microwave radiation to the treatment site. As mentioned above, the microwave source may even be placed outside of the patient's body in some cases.

FIG. 19 assumes a single source 1907 of microwave radiation 1906 directed along a single path to the carbon particle 1902 included in the thermal target material. If all of the microwave energy needed for absorption by carbon particle 1902 is applied along this single path, all of the microwave energy will have to traverse the path and thus the cells located between the microwave source 1907 and the carbon particle. In order to reduce the microwave radiation that must be applied along a single path to the carbon material, it may be desirable in some cases to apply microwave energy directionally from two or more different sources. This technique essentially divides the total microwave energy so that it is distributed among the paths, reducing the amount of microwave energy along each path while still delivering the total microwave energy needed at the treatment site for absorption by the carbon particles.

Figure 20:
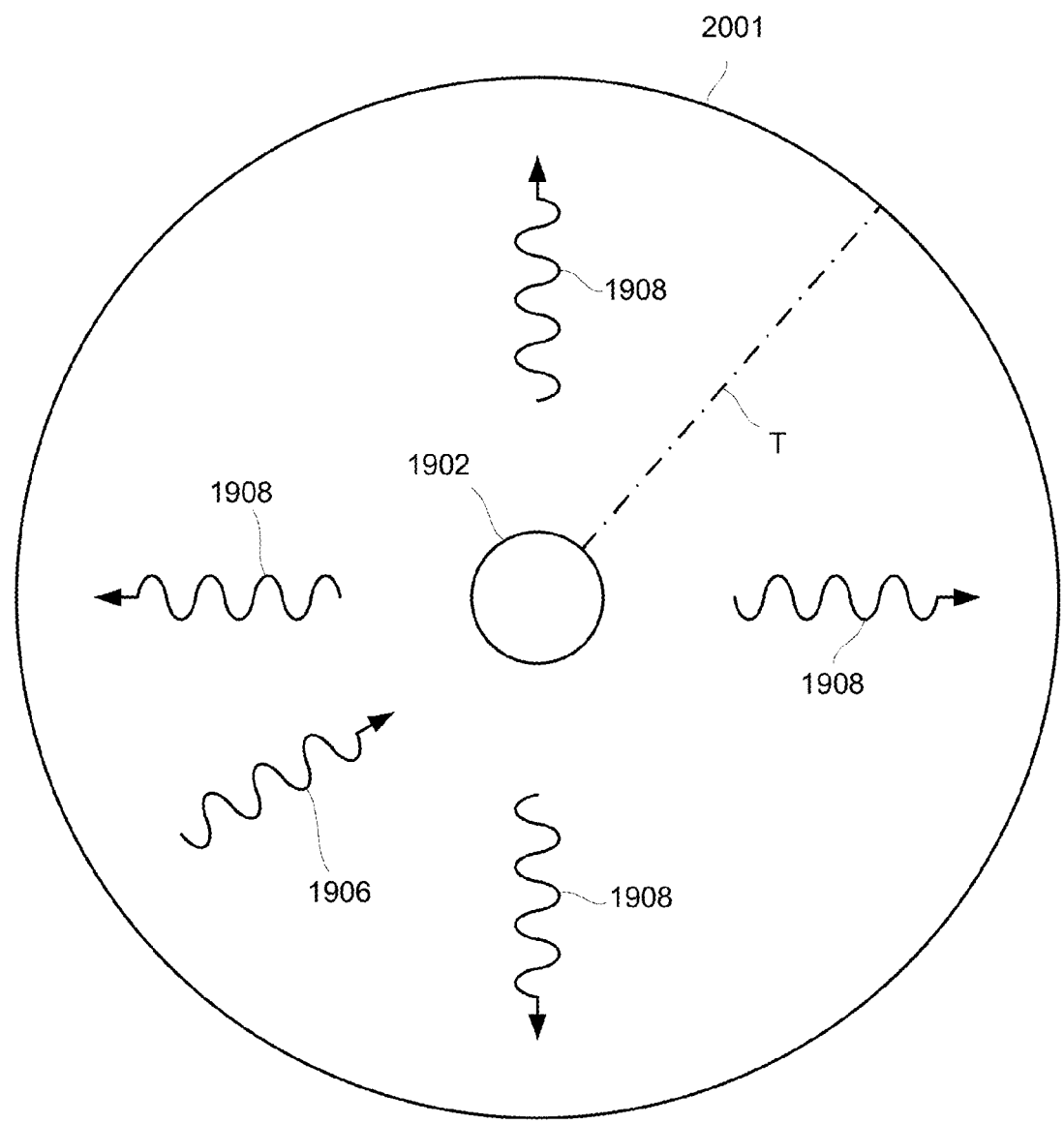
FIG. 20 is a conceptual representation showing a carbon particle and effective treatment range for the carbon particle.

FIG. 20 shows a conceptual representation of carbon particle 1902 found in a thermal target material according to the present invention, along with an effective treatment range T and treatment boundary 2001 from the carbon particle. The effective treatment range T from carbon particle 1902 is the range within which the desired heat energy is radiated from the carbon particle for the given incident microwave radiation. This effective treatment range T is limited by the power level of the microwave radiation that is incident on carbon particle 1902, and the power level of the incident microwave radiation is limited as described in connection with FIG. 19. Given these constraints, one application of the invention first determines the effective treatment range T or the heat energy that must be radiated from the carbon particles in order to produce the desired temperature increase in the cells to be treated, and then, based on the heat energy that is anticipated to be required for the desired treatment, determine the microwave energy that must be incident on the carbon particles and the particle dispersion pattern required in order to radiate that heat energy. With this microwave energy in mind for the given application and the microwave absorption characteristics known for the biological tissues through which the microwave energy must pass, the required microwave emission energy may be determined for the given application. If the microwave emission energy is too high for an emission source (antenna assembly) placement outside of the patient's body, then it must be determined whether a closer placement of the microwave emission source to the thermal target material is possible. Regardless of whether the microwave emission source is located outside of the patient's body or within the patient's body, treatment methods according to the present invention preferably utilize the lowest possible microwave energy emission that is necessary to produce the desired heating effect in the desired biological tissue from heat energy radiated from the carbon particles in the thermal target material.

The above described preferred embodiments are intended to illustrate the principles of the invention, but not to limit the scope of the invention. Various other embodiments and modifications to these preferred embodiments may be made by those skilled in the art without departing from the scope of the present invention.

As used herein, whether in the above description or the following claims, the terms "comprising," "including," "carrying," "having," "containing," "involving," and the like are to be understood to be open-ended, that is, to mean including but not limited to. Any use of ordinal terms such as "first," "second," "third," etc., in the claims to modify a claim element does not by itself connote any priority, precedence, or order of one claim element over another, or the temporal order in which acts of a method are performed. Rather, unless specifically stated otherwise, such ordinal terms are used merely as labels to distinguish one claim element having a certain name from another element having a same name (but for use of the ordinal term).

The invention claimed is:

1. A method of treatment for biological tissues, the method including:
 (a) positioning an effective amount of a thermal target material at a treatment site of a patient, the treatment site comprising a location adjacent to biological tissue to be treated, and the thermal target material including carbon molecules produced from a liquid reactant process in which a carbon bearing feed material is contacted with a liquid reactant material; and (b) directing an effective quantity of microwave energy to the thermal target material, the effective quantity of microwave energy being a quantity at a given wavelength sufficient to heat biological tissue adjacent to the treatment site to a treatment temperature.

2. The method of claim 1 wherein the treatment site encompasses diseased tissue to be denatured and the treatment temperature is a minimum temperature at which the diseased tissue is denatured.

3. The method of claim 1 wherein the treatment site encompasses damaged tissue and the treatment temperature is a minimum temperature at which repair processes in the damaged tissue are temperature enhanced.

4. The method of claim 1 wherein the carbon bearing feed material includes acetylene and the carbon molecules include generally spherical carbon nanostructures.

5. The method of claim 1 wherein the thermal target material includes the carbon molecules in a carrier liquid.

6. The method of claim 5 wherein the carbon bearing feed material includes acetylene and the carbon molecules include generally spherical carbon nanostructures.

7. The method of claim 1 wherein heating provided by interaction between the effective quantity of microwave energy and biological tissue located between an emitter for the microwave energy and the treatment site is insufficient to denature the biological tissue located between the emitter and the treatment site.

8. A thermal target material for use in the thermal treatment of biological tissues, the thermal target material including:

(a) carbon molecules produced from a liquid reactant process in which a carbon bearing feed material is contacted with a liquid reactant material; and (b) a carrier fluid.

9. The material of claim 8 wherein the carrier fluid includes a viscosity enhancing agent.

10. The material of claim 8 wherein the carbon bearing feed material includes acetylene and the carbon molecules include generally spherical carbon nanostructures.

11. The material of claim 8 wherein the carbon bearing feed material includes acetylene.

12. A thermal target material for use in the thermal treatment of biological tissues, the thermal target material including:

(a) carbon molecules which are substantially free of chemically bound hydrogen; and (b) a carrier fluid.

13. The material of claim 12 wherein the carrier fluid includes a viscosity enhancing agent.

14. The material of claim 12 wherein the carbon molecules include generally spherical carbon nanostructures.

15. A method of treatment for biological tissues, the method including:

(a) positioning an effective amount of a thermal target material at a treatment site of a patient, the treatment site comprising a location adjacent to biological tissue to be treated;

(b) directing an effective quantity of microwave energy from a microwave emitter to the thermal target material, the effective quantity of microwave energy being a quantity at a given wavelength sufficient to heat biological tissue adjacent to the treatment site to a treatment temperature; and (c) wherein the thermal target material includes carbon molecules which absorb the microwave energy such that heat energy radiated from the thermal target material in response to the microwave energy is sufficient to heat the biological tissue adjacent to the treatment site to the treatment temperature while heat energy released in an interaction between the microwave energy and biological tissue located between the microwave emitter and the treatment site is insufficient to denature the biological tissue located between the microwave emitter and the treatment site.

16. The method of claim 15 wherein the biological tissue adjacent to the treatment site comprises diseased tissue to be denatured and the treatment temperature is a minimum temperature at which the diseased tissue is denatured.

17. The method of claim 15 wherein the biological tissue adjacent to the treatment site comprises damaged tissue and the treatment temperature is a temperature at which repair processes in the damaged tissue are temperature enhanced.

18. The method of claim 15 wherein the carbon molecules are produced from a reaction of acetylene with a reactant material.

19. The method of claim 18 wherein the carbon molecules include spherical carbon nano structures.

20. The method of claim 15 wherein the thermal target material includes the carbon molecules in a carrier liquid.

* * * * *